(12) United States Patent
Aguera et al.

(10) Patent No.: US 11,141,468 B2
(45) Date of Patent: Oct. 12, 2021

(54) METHOD OF TREATING A MAMMAL, INCLUDING HUMAN, AGAINST CANCER USING METHIONINE AND ASPARAGINE DEPLETION

(71) Applicant: ERYTECH PHARMA, Lyons (FR)

(72) Inventors: Karine Aguera, Lyons (FR); Willy Berlier, Lyons (FR); Fabien Gay, Lyons (FR); Yann Godfrin, Lyons (FR)

(73) Assignee: ERYTECH PHARMA, Lyons (FR)

( * ) Notice: Subject to any disclaimer, the term of this patent is extended or adjusted under 35 U.S.C. 154(b) by 171 days.

(21) Appl. No.: 16/067,398

(22) PCT Filed: Jan. 2, 2017

(86) PCT No.: PCT/EP2017/050006
§ 371 (c)(1),
(2) Date: Jun. 29, 2018

(87) PCT Pub. No.: WO2017/114966
PCT Pub. Date: Jul. 6, 2017

(65) Prior Publication Data
US 2019/0000941 A1    Jan. 3, 2019

(30) Foreign Application Priority Data

Dec. 31, 2015  (EP) .................................... 15307197

(51) Int. Cl.
| | |
|---|---|
| *A61K 38/54* | (2006.01) |
| *A61K 38/50* | (2006.01) |
| *A61K 38/51* | (2006.01) |
| *A61K 9/10* | (2006.01) |
| *A61K 35/18* | (2015.01) |
| *A61K 9/00* | (2006.01) |
| *A61K 31/675* | (2006.01) |
| *A61P 35/00* | (2006.01) |

(52) U.S. Cl.
CPC ............ *A61K 38/54* (2013.01); *A61K 9/0019* (2013.01); *A61K 31/675* (2013.01); *A61K 35/18* (2013.01); *A61K 38/50* (2013.01); *A61K 38/51* (2013.01); *A61P 35/00* (2018.01); *C12Y 305/01001* (2013.01); *C12Y 404/01011* (2013.01)

(58) Field of Classification Search
CPC .. A61K 2300/00; A61K 31/675; A61K 38/50; A61K 38/51; A61K 35/18; A61K 38/54; A61K 9/0019; A61K 9/10; A61P 35/00; C12Y 305/01001; C12Y 404/01011
See application file for complete search history.

(56) References Cited

U.S. PATENT DOCUMENTS

| 5,715,835 | A | * | 2/1998 | Lishko | ................. A61K 31/337 128/898 |
|---|---|---|---|---|---|
| 6,017,962 | A | | 1/2000 | Schold et al. | |
| 8,617,840 | B2 | | 12/2013 | Godfrin | |
| 10,273,444 | B2 | | 4/2019 | Godfrin | |
| 2004/0006028 | A1 | * | 1/2004 | Platz | ....................... A61P 35/02 514/43 |
| 2005/0234009 | A1 | * | 10/2005 | Johnson | .................. A61P 35/00 514/45 |
| 2007/0149571 | A1 | * | 6/2007 | Stein | .................. A61K 2300/00 514/321 |
| 2008/0261262 | A1 | | 10/2008 | Godfrin | |
| 2010/0284982 | A1 | | 11/2010 | Yang et al. | |
| 2013/0302400 | A1 | * | 11/2013 | Maneval | ................. A61K 31/37 424/450 |
| 2014/0154797 | A1 | | 6/2014 | Godfrin | |
| 2015/0086521 | A1 | | 3/2015 | Godfrin | |
| 2016/0095884 | A1 | | 4/2016 | Godfrin et al. | |
| 2016/0243262 | A1 | | 8/2016 | Ortac et al. | |
| 2016/0361361 | A1 | | 12/2016 | Godfrin et al. | |

OTHER PUBLICATIONS

Ashraf S. El-Sayed and Ahmed A. Shindia (2011). PLP-Dependent Enzymes: a Potent Therapeutic Approach for Cancer and Cardiovascular Diseases, Targets in Gene Therapy, Prof. Yongping You (Ed.), ISBN: 978-953-307-540-2, pp. 119-146, Published online Aug. 23, 2011.
Emilie Thivat et al. "Phase II Trial of the Association of a Methionine-free Diet with Cystemustine Therapy in Melanoma and Glioma.", 2009, pp. 5235-5240, Anticancer Research 29: Issue 12.
Sun X. et al. "In vivo efficacy of recombinant methioninase is enhanced by the combination of polyethylene glycol conjugation and pyridoxal 5'-phosphate supplementation.", Dec. 1, 2003, pp. 8377-8383, vol. 62, No. 23, Cancer Res. 2003.
Ashraf S El-Sayed: "Microbial l-methioninase: production, molecular characterization, and therapeutic applications", Applied Microbiology and Biotechnology, Springer, Berlin, DE, vol. 86, No. 2, Feb. 10, 2010 (Feb. 10, 2010), pp. 445-467, XP019799866, ISSN: 1432-0614 p. 461-p. 463.
International Search Report for PCT/EP2017/050006, completed Feb. 8, 2017.
Written Opinion of the International Searching Authority for PCT/EP2017/050006, completed Feb. 8, 2017.
Durando, et al, "Dietary Methionine Restriction with FOLFOX Regimen as First Line Therapy of Metastatic Colorectal Cancer: A Feasibility Study" Apr. 26, 2010, pp. 205-209, vol. 78, Oncology 2010.

(Continued)

*Primary Examiner* — Blaine Lankford
(74) *Attorney, Agent, or Firm* — B. Aaron Schulman, Esq.; Stites & Harbison, PLLC

(57) ABSTRACT

The invention is related to a new method for treating liquid and solid cancers, in a mammal, including human, wherein methioninase is administered before asparaginase. The invention also encompasses the use of a dietary methionine deprivation, possibly combined with methioninase administration, in advance of asparaginase treatment. Methioninase and asparaginase may be used in particular under free form, pegylated form or encapsulated into erythrocytes.

9 Claims, 4 Drawing Sheets

(56) References Cited

OTHER PUBLICATIONS

Abakumova, et al., "Antitumor Activity of L-Asparaginase from Ervinia carotovora against Different Human and Animal Leukemic and Solid Tumor Cell Lines", 2012, pp. 308-316, vol. 6, No. 4, Biochemistry Supplement Series B: Biomedical Chemistry.
Covini, et al., "Expanding Targets for a Metabolic Therapy of Cancer: L-Asparaginase", 2012, pp. 4-13, vol. 7, Recent Patents on Anti-Cancer Drug Discovery.
Hui-Yan, Guo, et al., "Expression of the Biochemical Defect of Methionine Dependence in Fresh Patient Tumors in Primary Histoculture", Jun. 1, 1993, pp. 2479-2483, vol. 53, Cancer Research.

\* cited by examiner

METHOD OF TREATING A MAMMAL, INCLUDING HUMAN, AGAINST CANCER USING METHIONINE AND ASPARAGINE DEPLETION

The present invention is related to a new method, particularly enzymatic method of treating a mammal, including human, against cancer, and to novel uses of asparaginase and methioninase in the treatment of cancer. Enzymatic therapies are intended to starve tumours and help in particular manage cancers.

BACKGROUND OF THE INVENTION

Asparaginase hydrolyses and depletes asparagine, an amino acid essential for the production of the proteins necessary for cell life. Now, in contrast to normal cells, certain cancerous lymphoblastic cells do not have the capacity to produce their asparagine themselves and are dependent on extra-cellular sources for the synthesis of their proteins. The enzyme may thus be used to treat Leukemias (liquid or blood cancers). L-asparaginase has thus been used in chemotherapy combination for the treatment of Acute Lymphoblastic Leukemia (ALL) for the last thirty years. ERY-ASP consists of red blood cell-encapsulated L-asparaginase. Encapsulation enables L-asparaginase to destroy asparagine inside the red blood cell, preventing allergic reactions and reducing other adverse events (WO 2006/016247, incorporated herein by reference).

Methionine-γ-lyase (MGL; EC number 4.4.1.11; CAS number 42616-25-1), also designated as methioninase, is a pyridoxal-dependent enzyme involved in the metabolism of L-methionine (Met), an essential, sulfur-containing proteinogenic amino acid. Met requirement in cancers has been purposed in the 1970s: studies revealed that substitution of Met by its precursor homocysteine in culture medium has no impact on normal cells such as fibroblasts but leads to a slow growing rate of several transformed or malignant cells. In PC-3 prostate cancer cells, anti-tumor effects of Met starvation were also reinforced by using a Met analogue which dramatically slowed the proliferation of cancer cells both in vitro and in vivo and forced cells to enter apoptosis. Complementary studies revealed that exogenous Met restriction in Met-dependent cancer cells blocks cell division in the late S or G2 phase of the cell cycle. As Met restriction appeared to be effective for cancer treatment, therapeutic approach using MGL enzyme from several sources was investigated for Met depletion in the tumor microenvironment. The aim was to develop a new therapeutic solution based on MGL encapsulated into erythrocytes for systemic depletion of Met in patients harbouring Met-dependent cancers (WO 2015/121348, incorporated herein by reference).

SUMMARY OF INVENTION

There is still a need for new or additional therapeutic solutions in cancer treatment.

The effect of drug combination is inherently unpredictable. There is often a propensity for one drug to partially or completely inhibit the effects of the other. In vitro studies were carried out to assess cytotoxic effects of the enzymes constituting ERY-ASP and ERY-MET, L-asparaginase and MGL, alone or in combination, on a selected human leukemia cell line (HL-60). For each drug separately, the concentration that gives a 50% inhibition of cell viability (IC50) was previously determined. Then, assays were performed to evaluate the benefits of treatment combination when some delay, e.g. 72 hours were added between the additions of L-asparaginase and MGL (IC50 dose for each enzyme), whatever the order of combination.

The present invention is based on the surprising observation that cell mortality could be increased with an addition of MGL at IC50 dose followed by L-asparaginase at IC50 dose 3 days later. The reverse design of enzyme addition did not permit to obtain such increase of cell mortality in vitro in a liquid tumor model, say a leukemia model. This remarkable effect has been confirmed in a solid tumor, say gastric tumor, wherein an increase of cell mortality in vitro and tumor volume regression in vivo were observed. Without willing to be bound by theory, it can be hypothesized that methionine deprivation induced by MGL activity could make the cells more responsive to L-asparaginase and that there is probably a link with the role of each enzyme involved in the cell cycle regulation. This finding opens the way to treatment regimens comprising sequential methionine deprivation or methioninase treatment and asparagine deprivation or asparaginase treatment. As it will be evident from the following disclosure, the invention may encompass diet and/or drug administration that induces the beneficial effect on cancer. Thus the invention may combine diet and drug administration, in any combination wherein methionine deprivation or methioninase treatment precedes asparagine deprivation or asparaginase treatment. As methioninase is also known as having a cysteinase activity, and asparaginase as having a glutaminase activity, it cannot be excluded that a cysteinase activity, respectively a glutaminase activity may be involved in the mode of action of methioninase, respectively asparaginase.

An object of the invention is a method for treating cancer in a mammal in need thereof, the method comprising depriving the mammal for methionine, then depriving the mammal for asparagine. What is searched for is to reduce the amount of methionine and asparagine available to the cancer cells. As it will be apparent from the foregoing, methionine deprivation may be performed through dietary methionine deprivation and/or methioninase administration, whereas asparagine deprivation may preferably be performed using asparaginase ad ministration.

By deprivation, it is meant a sufficient reduction of methionine or asparagine to produce beneficial effects in treating cancer, the cancer cells being deprived for sufficient amount of the amino acid.

By enzyme treatment, it is meant that the enzyme will degrade the concerned amino acid and possibly induce other beneficial effects such as inhibition of protein or amino acid synthesis or any mechanism that leads to lack of sufficient amount of the amino acid to the cancer cell.

An object of the present invention is a pharmaceutical composition for use in treating cancer in a mammal comprising asparaginase and methioninase for at least one sequential administration with methioninase being administered before asparaginase. As asparaginase and methioninase are to be administered separately and sequentially, the composition may be qualified of set or kit comprising separate formulations thereof or of compositions to be used in accordance with order and frequence of the invention.

In the context of the invention under its different aspects or objects, at least one sequential administration means that the same mammal may be treated sequentially more than once during a treatment therapy or phase. However, one or several methioninase administration(s) may be performed before one or several asparaginase administration(s).

Another object of the present invention is the use of asparaginase and methioninase for the preparation of a pharmaceutical composition or pharmaceutical compositions or a kit or set of pharmaceutical compositions (one containing methioninase, another one containing asparaginase), wherein the composition(s) or the kit is for use in treating cancer in a mammal with at least one sequential administration with methioninase being administered before asparaginase.

Other objects of the invention are:
- a pharmaceutical composition comprising asparaginase for use in treating cancer in a mammal, wherein the composition is to be administered to a mammal that has been administered methioninase;
- a pharmaceutical composition comprising asparaginase for use in treating cancer in a mammal, wherein the composition is to be administered to a mammal that has been subjected to methionine deprivation diet, i.e. has been administered a methionine deprived food, therapeutic or not; by therapeutic food in the meaning of this invention, it is meant a food administered in medical environment and/or subjected to marketing authorization by Regulatory Authority, especially a liquid food, that may be or not administered by infusion;
- a pharmaceutical composition comprising methioninase for use in treating cancer in a mammal, wherein the composition is to be administered to a mammal that will be further administered asparaginase;
- a food composition or diet, therapeutic or not, comprising no methioninase or substantially no methionine for use in depriving a mammal for methionine, before treating the mammal with asparaginase.

Other objects of the invention are:
- the use of asparaginase for the preparation of a pharmaceutical composition for use in treating cancer in a mammal, wherein the composition is to be administered to a mammal that has been administered methioninase;
- the use of asparaginase for the preparation of a pharmaceutical composition for use in treating cancer in a mammal, wherein the composition is to be administered to a mammal that has been subjected to methionine deprivation diet, i.e. has been administered a methionine deprived food, therapeutic or not;
- the use of methioninase for the preparation of a pharmaceutical composition for use in treating cancer in a mammal, wherein the composition is to be administered to a mammal that will be further administered asparaginase.

Still another object of the invention is a kit comprising a pharmaceutical composition containing methioninase or a therapeutic food or diet for methionine deprivation, and a pharmaceutical composition containing asparaginase, the compositions being separately packaged. The compositions are for sequential administration with methioninase or food/diet being administered before asparaginase. The kit may further contain a leaflet indicating that the compositions are for sequential administration with methioninase or food/diet being administered before asparaginase.

Still another object of the invention is a method of treatment of cancer in a mammal comprising administering to a mammal first an efficient amount of methioninase and second an efficient amount of asparaginase.

Still another object of the invention is a method of treatment of cancer in a mammal comprising administering to a mammal first a food or diet, therapeutic or not, to deprive methionine, and second an efficient amount of asparaginase.

Still another object of the invention is a method of treatment of cancer in a mammal having a low methionine bioavailable level, or having been subjected to a food or diet, therapeutic or not, having deprived methionine, the method comprising administering to the mammal an efficient amount of asparaginase.

In these different objects, methioninase administration and methionine diet deprivation may be combined.

The invention may be beneficial to any cancer, including liquid, i.e. haematological cancers, and solid cancers.

A specific object of the invention is the application of this invention to the treatment of cancers auxotrophic to asparagine and/or methionine.

A specific, object of the invention is the application of this invention to the treatment of cancers not auxotrophic to asparagine and/or methionine.

The invention may apply to any mammal and especially human, companion animals such as dogs and cats and sport animals such as horses.

DETAILED DESCRIPTION

The person skilled in the art may understand from the present disclosure that the duration of treatment with diet or one of the drugs, and the delay between methionine deprivation and asparaginase treatment, may vary depending on the treatment, on the patient response and importantly on the half-life of the drug or diet effect. There may be a difference depending on the dosage form used in the invention, for example a free enzyme, a pegylated enzyme and erythrocytes encapsulating the enzyme, or else enzyme bound to microcapsules (e.g. made of PLA or PLGA) or liposomes or encapsulated in these structures.

In a preferred embodiment of these different objects, the delay between the end of methioninase administration and the initiation of asparaginase administration is between about 1 h and about 7 days, in particular between about 3 h and about 6 days, preferably between about 1 day and about 5 days. Preferably, in this embodiment, methioninase is under free form or pegylated form, and asparaginase may be under any of the forms described herein.

In another embodiment, the delay between the end of methioninase administration and the initiation of asparaginase administration is between about 1 h and about 30 days, in particular between about 1 day and about 20 days, preferably between about 1 day and about 10 days. Preferably, in this embodiment, methioninase is encapsulated, preferably into erythrocytes, and asparaginase may be under any of the forms described herein.

In still another embodiment, the delay between the end of methionine restriction and the initiation of asparaginase administration is between about 1 h and about 7 days, in particular between about 1 h and about 0.3 days, preferably between about 1 h and about 1 day. Asparaginase may be under any of the forms described herein.

Compositions Comprising Enzyme Under Free Form or Under Pegylated Form, and the Like:

These compositions can be administered to a mammal using standard techniques. Techniques and formulations generally may be found in Remington's Pharmaceutical Sciences, 18.sup.th ed., Mack Publishing Co., Easton, Pa., 1990 (hereby incorporated by reference).

Pharmaceutically acceptable carriers and/or excipients can also be incorporated into a pharmaceutical composition according to the invention to facilitate administration of the particular methioninase or asparaginase. Examples of carriers suitable for use in the practice of the invention include calcium carbonate, calcium phosphate, various sugars such as lactose, glucose, or sucrose, or types of starch, cellulose derivatives, gelatin, vegetable oils, polyethylene glycols, and physiologically compatible solvents. Examples of physiologically compatible solvents include sterile solutions of water for injection (WFI), saline solution and dextrose.

Pharmaceutical compositions according to the invention can be administered by different routes, including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g. intramuscular, intravenous, intraperitoneal, and subcutaneous injection. For injection, pharmaceutical compositions are formulated in liquid solutions, preferably in physiologically compatible buffers or solutions, such as saline solution, Hank's solution, or Ringer's solution. In addition, the compounds may be formulated in solid form and redissolved or suspended immediately prior to use. For example, lyophilized forms of the methioninase or asparaginase can be used.

Systemic administration can also be accomplished by transmucosal or transdermal means. For transmucosal or transdermal administration, penetrants appropriate to the barrier to be permeated are used in the formulation. Such penetrants are well known in the art, and include, for example, for transmucosal administration, bile salts, and fusidic acid derivatives. In addition, detergents may be used to facilitate permeation. Transmucosal administration, for example, may be through nasal sprays, inhalers (for pulmonary delivery), rectal suppositories, or vaginal suppositories. For topical administration, compounds can be formulated into ointments, salves, gels, or creams, as is well known in the art.

The invention encompasses also the use of implanted devices or applied on the mammal to deliver the enzyme, for instance through infusion or another route. In a special embodiment, the device comprises two chambers or vials, one containing methioninase, the other containing asparaginase. The device has, for each chamber or vial, a tube and the like for delivering the enzyme into the blood circulation, an electronic or electrical valve or pump, or an actuated piston, that is controlled by an electronic circuit and a suitable software. The electronic circuit and its software controls the delivery of methioninase first, during a predetermined period of time, preferably at a certain debit rate, a delay period, and then the delivery of asparaginase, during a predetermined period of time, preferably at a certain debit rate.

Compositions Comprising Erythrocytes (Red Blood Cells or RBCs) Encapsulating the Enzyme:

In an embodiment, asparaginase is encapsulated inside erythrocytes and the composition comprises a suspension of these erythrocytes in a pharmaceutically acceptable carrier or vehicle.

In an embodiment, methioninase is encapsulated inside erythrocytes and the composition comprises a suspension of these erythrocytes in a pharmaceutically acceptable carrier or vehicle:

In an embodiment, asparaginase is in free form or under a pegylated form (PEG-asparaginase), in a pharmaceutically acceptable carrier or vehicle.

In an embodiment, methioninase is in free form or under a pegylated form (PEG-methioninase), in a pharmaceutically acceptable carrier or vehicle.

In an embodiment, methioninase is administered in an amount of between about 100 and about 100 000 IU, in particular between about 500 and about 50 000 IU, preferably between about 500 and about 5000 IU.

In an embodiment, asparaginase is administered once in an amount of between about 500 and about 100 000 IU, in particular between about 1000 and about 50 000 IU, preferably between about 5000 and about 30 000 IU.

In an embodiment, the composition is for use for two or more sequential administrations, especially 2 or 3.

In an embodiment, asparaginase and methioninase are used sequentially in accordance with the invention, and these enzymes are both encapsulated into erythrocytes.

In an embodiment, asparaginase and methioninase are used sequentially in accordance with the invention, with asparaginase encapsulated into erythrocytes and methioninase in free form or under a pegylated form.

In an embodiment, asparaginase and methioninase are used sequentially in accordance with the invention, with methioninase encapsulated into erythrocytes and asparaginase in free form or under a pegylated form.

"Encapsulated" means that the enzyme is contained inside the erythrocytes. It is possible however that some minor amount of enzyme is retained within the erythrocyte wall.

Dietary Methionine Restriction:

Dietary methionine restriction has been proposed either in association with cystemustine therapy in melanoma and glioma (E. Thivat et al., Anticancer Research 2009, 29: 5235-5240) or with FOLFOX as first line therapy of metastatic colorectal cancer (X. Durando et al., Oncology 2010, 78: 205-209). Methionine restriction or deprivation diet is a food regimen or feeding the mammal with a food composition during a sufficient time to induce a full or substantial decrease or elimination of free methionine in the mammal.

The food may preferably be a liquid food that is administered through parenteral route, especially infusion.

Also, methionine deprivation using methioninase aims at inducing a full or substantial decrease or elimination of free methionine in the mammal. Typically, this diet is performed in order to decrease the methionine level of 30 to 100%, typically from 30 to 60% with respect to the mean level in the mammal. Reference may be done to the works by Thivat 2009 and Durando 2010.

Administration of the food may be done during one day or more, for example from one day to seven days.

In an embodiment, the food is combined to methioninase treatment, for example the food is administered during the whole or part duration of treatment with methioninase.

Methioninase

Methioninase is further called, inter alia, L-methioninase, Methionine Gamma Lyase MGL; this compound is receiving number EC 4.4.1.11 and CAS number 42616-25-1. In order to be aware of the methioninase sources which may be used according to the invention, mention may notably be made to the publication El Sayed A, Applied Microbiol. Biotechnol. (2010) 86: 445-467.

A recombinant methioninase may be produced in the *Escherichia coli* bacterium from a gene coding for the enzyme, for example from the *Pseudomonas putida* bacterium. The thereby obtained enzyme called rMETase may be used under free form or under a modified form, e.g. pegylated form (PEG-rMETase). See X. Sun et al. Cancer Research 2003, 63: 8377-8383. It may also be encapsulated into erythrocytes, the composition or suspension advantageously containing an amount of erythrocytes and an amount of encapsulated methioninase that is sufficient to deliver to the patient the dose of asparaginase that has been decided.

The person skilled in the art may refer to WO 2015/121348 for compositions and methods of use.

The composition of methioninase may further comprise the cofactor of the enzyme, i.e. PLP, and/or a precursor thereof, which may be a non-phosphate precursor, such as a non-phosphate form of vitamin B6, and/or a phosphate precursor such as pyridoxine phosphate (PNP).

Vitamin B6 exists in different forms, either phosphate or non-phosphate. Pyridoxine phosphate (PNP), pyridoxal phosphate (PLP) and pyridoxamine phosphate (PMP) are the phosphate forms thereof. The corresponding non-phosphate forms are pyridoxine (PN), pyridoxal (PL), and pyridoxamine (PM). The non-phosphate forms of vitamin B6 may cross the erythrocyte membrane, which the phosphate forms can only cross with difficulty. According to the predominant route, pyridoxine (PN) is transformed inside the erythrocytes into PNP under the effect of PN-kinase, PNP is then transformed into PLP under the effect of PNP-oxidase. The PLP may then be transformed into pyridoxal (PL) under the effect of PLP-phosphatase and the PL may leave the erythrocytes. It is easily understood that the provided precursor is able to undergo transformations in the erythrocytes during the preparation method or during the storage of the composition.

By a non-phosphate form of vitamin B6, will be meant here one of the three "vitamers" of vitamin B6 or a mixture of two or three vitamers: PL, PN and PM. The PN form is preferred. They may also be in the form of a salt.

The composition may comprise PLP encapsulated in erythrocytes. The PLP may be provided during the encapsulation procedure or be totally or partly obtained in the erythrocytes from its precursor. The PLP either present or formed may be associated with the enzyme. The composition may therefore comprise the corresponding holoenzyme, for example methioninase-PLP. Under these conditions, the half-life of the active enzyme, as observed for example with the duration of the plasma depletion of its substrate, is considerably increased. The composition according to the invention notably gives the possibility of preserving enzymatic activity beyond 24 hours after administration, notably at or beyond 1, 5, 10 or 15 days.

In an embodiment, the composition of methioninase therefore comprises pyridoxal phosphate (PLP) and/or a non-phosphate form of vitamin B6 and/or a phosphate precursor, pyridoxine phosphate (PNP) and/or pyridoxamine phosphate (PMP).

According to a feature, PNP and/or PMP is encapsulated inside the erythrocytes within the composition. This precursor may be co-encapsulated with the enzyme or be totally or partly obtained in the erythrocytes from its own precursor.

The composition notably comprises from about 0.05 to about 600, notably from about 0.5 to about 100, preferably from about 5 to about 50 µmoles of PLP and/or PNP and/or PMP, encapsulated per liter (L) of red blood cells (erythrocytes).

According to a feature, the composition comprises erythrocytes encapsulating the PLP enzyme and PLP and further a non-phosphate PLP precursor, encapsulated in the erythrocytes, present inside the erythrocytes or present inside and outside the erythrocytes. This non-phosphate precursor may be PN, PL or PM, preferably PN, or a mixture of two or three of these compounds. The non-phosphate precursor may be present inside and/or outside the erythrocytes. The presence of this non-phosphate precursor gives the possibility of reaching a remarkably higher intra-erythrocyte PLP level than in the absence of this non-phosphate precursor.

In an embodiment, the composition comprises erythrocytes encapsulating the methioninase and in addition PLP and one of its phosphate precursors, PNP, PLP and/or PMP. This same composition may further comprise advantageously a non-phosphate precursor, notably PN, as this has just been described.

The composition or suspension advantageously contains an amount of erythrocytes and an amount of encapsulated methioninase that is sufficient to deliver to the patient the dose of methioninase that has been decided.

The composition may thus further comprise PLP or a PLP precursor for simultaneous, separate or sequential administration with the methioninase. In an embodiment, the composition comprises methioninase encapsulated inside erythrocytes and a non-phosphate precursor of PLP for separate or sequential administration.

According to an embodiment, the composition comprises (i) a formulation of erythrocytes and a pharmaceutically acceptable vehicle, the erythrocytes encapsulating methioninase, and (2i) a formulation of vitamin B6 in a non-phosphate form, preferably PN, and a pharmaceutically acceptable vehicle. These formulations are for simultaneous, separate or sequential administration, and dedicated to methionine depletion according to the invention. The method of use presented thereafter will detail the best modes of administration. The composition may notably be in the form of a set or kit, comprising separately these formulations. According to an embodiment, the pharmaceutically acceptable vehicle in the formulation of erythrocytes is a «preservation solution» for erythrocytes, i.e. a solution in which the erythrocytes encapsulating an active ingredient are suspended in their suitable form for being stored while awaiting their injection. A preservation solution preferably comprises at least one agent promoting preservation of the erythrocytes, notably selected from glucose, dextrose, adenine and mannitol. Possibly, the preservation solution contains inorganic phosphate allowing inhibition of the intra-erythrocyte PLP-phosphatase enzyme.

In an embodiment, methioninase encapsulated inside erythrocytes is to be administered at least once, preferably at least twice before asparaginase encapsulated inside erythrocytes is administered, and each methioninase administration is to be followed by administration of a solution of non-phosphate precursor of PLP before asparaginase is administered.

MGL activity is expressed in IU which corresponds to the amount of MGL required to liberate one micromole of ammonia per minute under the following conditions.

In the presence of its cofactor PLP, MGL hydrolyzes L-methionine into alpha-ketobutyric acid, forming one molecule of ammonium per molecule of L-methionine:

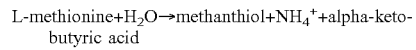
L-methionine+$H_2O \rightarrow$ methanthiol+$NH_4^+$+alpha-ketobutyric acid The dosage of MGL activity is performed at 37° C., pH=8.6, in presence of 0.26 µg/mL of MGL, 20 nM of PLP and 25 mM of L-methionine, a commercially available test may be used (e.g. $NH_3$ kit, Roche diagnostics).

The method consists in measuring the kinetics of ammonium production between 5 min and 10 min of the reaction, when maximum activity (Vmax) of MGL is reached. The measurement of ammonium production is obtained by measuring the variation of optical density at 340 nm due to the oxidation of NADPH to NADP⁺ by the glutamate deshydrogenase (GLDH) in the presence of ammonium and alpha-ketoglutaric acid, as follows:

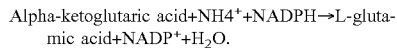
Alpha-ketoglutaric acid+NH4⁺+NADPH→L-glutamic acid+NADP⁺+H₂O.

Asparaginase

Asparaginase itself is designated by the CAS number: 9015-68-3. Its usual name is asparaginase; other common names for it are: colaspase, L-asparaginase and L-asparagine aminohydrolase.

The term asparaginase in the sense of the present invention covers asparaginase of any origin, it can in particular be of natural or recombinant origin, and any derivative incorporating asparaginase, such as for example a pegylated or PEG form (PEG-asparaginase), or a fragment retaining the activity of L-asparaginase. It also covers asparaginase whatever its bacterial origin. Thus, the asparaginase may be of the *E. coli* type, in particular E coil HAP-A-1-3, of the *Erwinia chrysanthemi* type or of the *Wolinella succinogenes* type. "Type" is understood to mean that it can be obtained from a culture of the bacterium in question or that it can be recombinant, in other words a form of asparaginase of that bacterium obtained by genetic engineering. In a preferred implementation mode, it is of the *E. coli* HAP-A-1-3 type.

Commercial products are available and usable herein: 5000 U Medac®, 10000 U Medac®, Oncaspar®. The product is under powder form, to be solubilized before use in an injectable liquid or water. Excipients may be present, such as sodium dihydrogenphosphate 1H₂O, sodium monohydrogenphosphate 7H₂O and/or sodium chloride.

The term asparaginase also covers asparaginase-like substances which in the sense of the invention are bacterial enzymes having an L-asparagine aminohydrolase activity. By way of example, Acinetobacter Glutaminase Asparaginase (AGA) may be cited.

According to an embodiment of the invention, asparaginase is encapsulated into erythrocytes and the composition or suspension advantageously contains an amount of erythrocytes and an amount of encapsulated asparaginase that is sufficient to deliver to the patient the dose of asparaginase that has been decided.

One IU asparaginase is defined as usualas the quantity of enzyme required to liberate 1 μmol ammonia per minute at pH 7.3 and 37° C. from L-asparagine, the quantity of L-asparaginase being in excess.

Encapsulation into Erythrocytes

According to an embodiment, the composition of methioninase and/or the composition of asparaginase comprises erythrocytes encapsulating the enzyme and a pharmaceutically acceptable vehicle. Preferably, the erythrocytes are issued from a mammal of the same species than the treated subject. When the mammal is a human, the erythrocytes are preferably of human origin. In an embodiment, the erythrocytes come from the patient itself.

According to an embodiment, the pharmaceutically acceptable vehicle is a «preservation solution» for erythrocytes, i.e. a solution in which the erythrocytes encapsulating the enzyme are suspended in their suitable form for being stored while awaiting their injection. A preservation solution preferably comprises at least one agent promoting preservation of the erythrocytes, notably selected from glucose, dextrose, adenine and mannitol.

The preservation solution may be an aqueous solution comprising NaCl, adenine and at least one compound from among glucose, dextrose and mannitol.

The preservation solution may comprise NaCl, adenine and dextrose, preferably an AS3 medium.

The preservation solution may comprise NaCl, adenine, glucose and mannitol, preferably a SAG-Mannitol or ADsol medium.

In particular, the composition or suspension, in a preservation solution, is characterized by an extracellular hemoglobin level maintained at a level equal to or less than 0.5, in particular 0.3, notably 0.2, preferably 0.15, even better 0.1 g/dl at 72 h and preservation at a temperature comprised between 2 and 8° C.

In particular, the composition or suspension, in a preservation solution, is characterized by an extracellular hemoglobin level maintained at a level equal to or less than 0.5, in particular 0.3, notably 0.2, preferably 0.15, even better 0.1 g/dl for a period comprised between 24 h and 20 days, notably between 24 and 72 h and preservation at a temperature comprised between 2 and 8° C.

The extracellular hemoglobin level is advantageously measured by the manual reference method described in G. B. Blakney and A. J. Dinwoodie, Clin. Biochem. 8, 96-102, 1975. Automatic devices also exist which allows this measurement to be made with a sensitivity which is specific to them.

In particular, the composition or suspension, in a preservation solution, is characterized by a hemolysis rate maintained at equal to or less than 2, notably 1.5, preferably 1% at 72 h and preservation at a temperature comprised between 2 and 8° C.

In particular, the composition or suspension, in a preservation solution, is characterized by a hemolysis rate maintained at equal to or less than 2, notably 1.5, preferably 1% for a period comprised between 24 h and 20 days, notably between 24 and 72 h and at a temperature comprised between 2 and 8° C.

Methods of Encapsulation

Encapsulating the enzymes into erythrocytes may be performed using an erythrocyte suspension that is put into contact with a hypotonic liquid medium resulting in the opening of pores in the erythrocyte membrane. There exist three alternatives in the lysis-resealing technique, which are hypotonic dialysis, hypotonic preswelling and hypotonic dilution, all based on the difference in osmotic pressure between the inside and the outside of the erythrocytes. Hypotonic dialysis is preferred.

The suspension of erythrocytes encapsulating the enzyme is notably able to be obtained with the following method:

1—suspending a pellet of erythrocytes in an isotonic solution at a hematocrit level equal to or greater than 65%, cooling between +1 and +8° C., 2—a lysis procedure, at a temperature maintained between +1 and +8° C., comprising the passing of the suspension of erythrocytes at a hematocrit level equal or greater than 65% and of a cooled hypotonic lysis solution between +1 and +8° C., into a dialysis device, such as a coil or a dialysis cartridge (the cartridge is preferred);

3—an encapsulation procedure by adding, preferably gradually, the enzyme to be encapsulated (notably in a solution made up beforehand) into the suspension before or during lysis, at a temperature maintained between +1 and +8° C.; and 4—a resealing procedure conducted in the presence of an isotonic or hypertonic, advantageously hypertonic solution, at a higher temperature, notably comprised between +30 and +42° C.

In a preferred alternative, use may be done of the method described in WO-A-2006/016247 (EP 1 773 452; which is incorporated herein by reference.):

1—suspending a pellet of erythrocytes in an isotonic solution at a hematocrit level equal to or greater than 65%, cooling between +1 and +8° C., 2—measuring osmotic fragility from a sample of erythrocytes from this same pellet, 3—a lysis procedure, at a temperature maintained between +1 and +8° C., comprising the passing of the suspension of erythrocytes at a hematocrit level equal to or greater than 65% and of a hypotonic lysis solution cooled between +1 and +8° C., into a dialysis device, such as a coil or a dialysis cartridge (the cartridge is preferred); the lysis parameters being adjusted according to the osmotic fragility measured earlier; notably, depending on the measured osmotic fragility, the flow of the erythrocyte suspension passing into the dialysis device is adjusted or the osmolarity of the lysis solution is adjusted; and 4—a procedure for encapsulation by adding, preferably gradually, the enzyme to be encapsulated (notably in a solution made beforehand) in the suspension before and during lysis, at a temperature maintained between +1 and +8° C.; and 5—a resealing procedure conducted in the presence of an isotonic or hypertonic, advantageously hypertonic solution, at a higher temperature, notably comprised between +30 and +42° C.

Notably, for dialysis, the pellet of erythrocytes is suspended in an isotonic solution with a high hematocrit level, equal to or greater than 65%, and preferably equal to or greater than 70%, and this suspension is cooled between +1 and +8° C., preferably between +2 and +6° C., typically around +4° C. According to a particular method, the hematocrit level is comprised between 65 and 80%, preferably between 70 and 80%.

When it is measured, the osmotic fragility is advantageously measured on erythrocytes just before the lysis step, in the presence or in the absence, preferably in the presence of the enzyme to be encapsulated. The erythrocytes or the suspension containing them are advantageously at a temperature close to, or identical with the temperature selected for lysis. According to another advantageous feature of the invention, the conducted measurement of the osmotic fragility is rapidly utilized, i.e. the lysis procedure is carried out in a short time after taking the sample. Preferably, this lapse of time between the sampling and beginning of lysis is less than or equal to 30 minutes, still better less than or equal to 25 and even to 20 minutes.

As regards to how to conduct the lysis-resealing procedure with measurement and taking into account of the osmotic fragility, one skilled in the art may refer for more details to WO-A-2006/016247. This document is incorporated herein by reference.

An improvement of this encapsulation technique was described in WO 2014/180897, to which one skilled in the art may refer and which is incorporated herein by reference. Thus, according to an embodiment, the erythrocytes encapsulating the enzyme, are obtained by a method comprising the encapsulation of the active ingredient inside erythrocytes by lysis-resealing, the obtaining of a suspension or of a pellet comprising erythrocytes incorporating the enzyme and a solution with an osmolality greater than or equal to 280 mOsmol/kg, in particular between about 280 and about 380 mOsmol/kg, preferably between about 290 and about 330 mOsmol/kg, the incubation of the pellet or of the suspension as such or after adding an incubation solution, at an osmolality greater than or equal to 280 mOsmol/kg, in particular between about 280 and about 380 mOsmol/kg, preferably between about 290 and about 330 mOsmol/kg. Incubation is notably carried out for a period greater than or equal to 30 minutes, in particular greater than or equal to 1 h. It is then proceeded with removal of the liquid medium of the incubated solution and the erythrocytes obtained are suspended in a solution allowing injection of the suspension into a patient, preferably a preservation solution allowing injection of the suspension into a patient. The indicated osmolality is that of the solution in which the erythrocytes are suspended or in a pellet at the relevant moment.

By «stabilized erythrocyte suspension», is notably meant a suspension having an extracellular hemoglobin content which remains less than or equal to 0.2 g/dl until its use in humans, the latter may intervene notably from 1 to 72 hours after producing the erythrocyte batch incorporating the active ingredient.

By «ready-to-use stabilized erythrocyte suspension», is meant the stabilized suspension in a solution allowing injection into a patient, notably in a preservation solution. Its hematocrit is generally equal to or greater than 35%, 40% or 45%.

By «erythrocyte pellet», is meant a concentrate or concentration of erythrocytes collected after separating the erythrocytes of the liquid medium in which they were suspended previously. The separation may be ensured by filtration or by centrifugation. Centrifugation is the means generally used for such a separation. A pellet comprises a certain proportion of liquid medium. Generally, the pellet has a hematocrit comprised between 70 and 85%.

By «incubation solution», is meant the solution in which the erythrocytes encapsulating an active ingredient are present during the incubation step. The incubation may be accomplished over a large range of hematocrits, notably between 10 and 85% of hematocrit.

By «fragile erythrocytes», are meant the erythrocytes stemming from the incorporation procedure which may, once suspended in a preservation solution, be lyzed when the suspension is preserved between 2 and 8° C., notably after 1 to 72 h.

By «initial hematocrit», is meant the hematocrit before cell loss due to lysis of the fragile erythrocytes during incubation.

The method may notably comprise the following steps:

(a) encapsulation of the enzyme inside erythrocytes, comprising the putting of the erythrocytes into contact with a hypotonic medium (allowing opening of pores in the membrane of the erythrocytes), the contacting with the active ingredient (for allowing it to enter the erythrocytes), the resealing of the erythrocytes, notably by means of an isotonic or hypertonic medium, advantageously hypertonic, (b) obtaining or preparing a suspension or pellet comprising erythrocytes incorporating the enzyme and a solution with an osmolality greater than or equal to 280 mOsmol/kg, in particular between about 280 and about 380 mOsmol/kg, preferably between about 290 and about 330 mOsmol/kg, (c) incubating the pellet or the suspension of step (b) as such or after adding an incubation solution, at an osmolality greater than or equal to 280 mOsmol/kg, in particular between about 280 and about 380 mOsmol/kg, preferably between about 290 and about 330 mOsmol/kg, for a period greater than or equal to 30 minutes, notably greater than or equal to 1 h, (d) removing the liquid medium of the incubated suspension of step (c), (e) suspending the erythrocytes obtained under (d) into a solution allowing injection of the suspension into a patient, preferably a preservation solution allowing injection of the suspension into a patient.

According to a first method, the step following the encapsulation by lysis-resealing, notably step (b), includes at least 1 washing cycle, preferably 2 or 3 washing cycles, by dilution of the obtained suspension or pellet in the lysis-resealing step or step (a) in a solution, at an osmolality greater than equal to 280 mOsmol/kg, in particular between about 280 and about 380 mOsmol/kg, preferably between about 290 and about 330 mOsmol/kg, and then obtaining a pellet of erythrocytes or a suspension. This pellet or this suspension comprises erythrocytes incorporating the enzyme and a solution with an osmolality greater than or equal to 280 mOsmol/kg, in particular between about 280 and about 380 mOsmol/kg, preferably between about 290 and about 330 mOsmol/kg. The following steps, e.g. (c), (d) and (e) are then applied.

According to a second method, in the lysis-resealing step or step (a), resealing of the erythrocytes by means of an isotonic or hypertonic medium produces the suspension of erythrocytes which may then be subject to incubation, e.g. the suspension of step (b), in a solution with an osmolality greater than or equal to 280 mOsmol/kg, in particular between about 280 and about 380 mOsmol/kg, preferably between about 290 and about 330 mOsmol/kg. In other words, the lysis-resealing step or step (a) includes a step for resealing the erythrocytes wherein the suspended erythrocytes encapsulating the enzyme are mixed with an isotonic or hypertonic resealing solution, advantageously hypertonic, producing a suspension of erythrocytes with an osmolality greater than or equal to 280 mOsmol/kg, in particular between about 280 and about 380 mOsmol/kg, preferably between about 290 and about 330 mOsmol/kg. In this method, the incubation step or step (c) comprises incubation of the suspension stemming from the resealing. The incubation is carried out for a period greater than or equal to 30 minutes, notably greater than or equal to 1 h. The following steps, e.g. (d) and (e) are then applied.

The steps, following the lysis-resealing, e.g. (b) to (e), are conducted under conditions resulting in the lysis of fragile erythrocytes, or of a majority of them, notably more than 50, 60, 70, 80 or 90%, or more. To do this, it is possible to act on the incubation period, the incubation temperature and on the osmolality of the solution in which the erythrocytes are suspended. The higher the osmolality, the longer the incubation time may be. Thus the lower the osmolality, the shorter may be the incubation in order to obtain the same effect. Also, the higher the temperature, the shorter the incubation time may be, and vice versa. One or several washing cycles will then allow removal of cell debris and extracellular hemoglobin, as well as the extracellular enzyme.

According to the invention, a washing cycle comprises the dilution of the suspension or pellet of erythrocytes, and then the separation between the erythrocytes and the washing solution. Preferably, a washing step comprises preferably 2 or 3 dilution-separation cycles. The separation may be achieved by any suitable means, such as filtration and centrifugation. Centrifugation is preferred.

Incubation is not limited by the hematocrit of the suspension. In this way, a suspension having an initial hematocrit generally comprised between 10 and 85%, notably between 40 and 80% may be incubated. This is rather referred to as a pellet from 70% and as a suspension below this value.

The removal step or step (d) aims at removing the liquid portion of the suspension or of the incubated pellet, in order to notably remove cell debris and the extracellular hemoglobin, as well as consequently the extracellular enzyme.

According to a first method for the removal step or step (d), separation, notably centrifugation is carried out, this being notably applicable to a suspension. This separation may be followed by one or several, for example 2 or 3, washing cycles, by dilution in an isotonic solution, and then separation, notably by centrifugation.

According to a second method for the removal step or step (d), dilution before separation notably centrifugation is carried out, this being applicable to a suspension or to a pellet. The dilution may notably be carried out with an isotonic washing solution or with a preservation solution.

The final step or step (e) consists of preparing the final suspension such that it may be administered to the patient, without any other treatment.

According to a first method for this step, a dilution of the erythrocyte pellet from the removal step or step (d) is carried out with the injection solution, notably the preservation solution.

According to a second method for this step, one or several cycles for washing the erythrocyte pellet stemming from the removal step or step (d) is carried out with the injection solution, notably the preservation solution, by dilution followed by separation. After washing, the erythrocytes are re-suspended in the injection solution, notably the preservation solution.

The method of the invention may further comprise one, several or the totality of the following features:

the incubation step or step (c) is carried out at a temperature comprised between about 2 and about 39° C., over sufficient time for ensuring lysis of fragile erythrocytes;

the incubation step or step (c) is carried out at a low temperature, notably comprised between about 2 and about 10° C., in particular between about 2 and about 8° C., and lasts for about 1 h to about 72 h, notably from about 6 h to about 48 h, preferably from about 19 h to about 30 h;

the incubation step or step (c) is conducted at a higher temperature comprised between about 20 and about 39° C., notably at room temperature (25° C.±5° C.) and lasts for about 30 min to about 10 h, notably from about 1 h to about 6 h, preferably from about 2 h to about 4 h; it is possible to operate at an even higher temperature than room temperature, but this may have a negative impact on the cell yield, P50 and/or the 2,3-DPG content;

in the incubation step or step (c), the suspension is at an initial hematocrit comprised between 10 and 85%, notably between 40 and 80%; a pellet from separation, having for example a hematocrit between 70 and about 85%, or a diluted pellet having a hematocrit comprised between about 40 and 70% may be incubated;

the incubation step comprises stirring of the suspension;

the incubation step does not comprise any stirring;

as a solution for washing and/or incubation, a metered aqueous NaCl solution is used for obtaining the desired osmolality; as an example, a solution may thus comprise 0.9% of NaCl; this solution may also comprise, notably in addition to NaCl, glucose, notably glucose monohydrate, monosodium phosphate dihydrate, disodium phosphate dodecahydrate; as an example, a composition comprises: 0.9% of NaCl, 0.2% of glucose monohydrate, 0.034% of monosodium phosphate dihydrate, 0.2% of disodium phosphate dodecahydrate;

the washing in the final step or step (e) is carried out with the preservation solution;

the osmolality of the solution (liquid portion) in the ready-to-use suspension or which may be injected into the patient is comprised between about 280 and about 380 mOsmol/kg, preferably between about 290 and about 330 mOsmol/kg;

the hematocrit of the ready-to-use suspension or which may be injected into the patient is equal to or greater than 35%, 40% or 45%;

all the steps for washing, incubation are carried out with the preservation solution;

the washing solution of step (b) and/or the washing solution of step (e) and the preservation solution are of the same composition and comprise compound(s) promoting preservation of the erythrocytes;

the preservation solution (and the washing solution(s) or the incubation solutions if necessary) is an aqueous solution comprising NaCl, adenine and at least one compound from among glucose, dextrose and mannitol;

the preservation solution (and the washing or incubation solution(s) if necessary) comprises NaCl, adenine and dextrose, preferably an AS3 medium;

the preservation solution (and the washing or incubation solution(s), if necessary) comprise NaCl, adenine, glucose and mannitol, preferably a SAG-Mannitol or ADsol medium.

The methods according to the invention notably comprise the following step:

(a) encapsulating the enzyme inside erythrocytes, comprising the contacting with a hypotonic medium allowing opening of pores in the membrane of the erythrocytes, the contacting with the enzyme in order to allow its entry into the erythrocytes, the resealing of the erythrocytes by means of an isotonic or hypertonic medium. It should be noted that the enzyme may be present in the suspension of erythrocytes before the lysis of the latter, or further be added during lysis or after lysis, but always before resealing. In an embodiment of this step (a), the method comprises the following sub-steps:

(a1) having a suspension of erythrocytes at a hematocrit equal to or greater than 60 or 65%, (a2) measuring the osmotic fragility of the erythrocytes in this suspension, (a3) a procedure for lysis and internalization of the active ingredient(s), comprising the passing of the erythrocyte suspension into a dialysis device, notably a dialysis cartridge, counter to a lysis solution, adjusting the flow of the erythrocyte suspension or adjusting the flow rate of the lysis solution or adjusting the osmolarity of the lysis solution, depending on the osmotic fragility measured under (a2), (a4) a procedure for resealing the erythrocytes.

Methods of Use

In a first aspect, the invention is a method for treating cancer in a mammal in need thereof, the method comprising depriving the mammal for methionine, then depriving the mammal for asparagine, especially through administering asparaginase in sufficient amount. What is searched for is to reduce the amount of methionine and asparagine available to the cancer cells. Methionine deprivation may be performed as mentioned above through dietary methionine deprivation and/or methioninase administration.

In a second aspect, the invention is a method for treating cancer in a mammal in need thereof, the method comprising administering, especially injecting, to the mammal in need thereof, a composition comprising methioninase and then a composition containing asparaginase.

Sequential administration, delay between methionine deprivation and/or methioninase administration, and asparaginase administration, dosages, repeated administrations and forms of pharmaceutical compositions (free form, pegylated form and/or suspension of erythrocytes (RBCs) encapsulating the enzyme) has been detailed above and apply to the methods of use.

In an embodiment, methioninase (e.g. under free form, pegylated form or encapsulated) is administered once or more.

In another embodiment, free or pegylated methioninase is administered more than once before asparaginase administration, for example two or more (e.g. 3, 4, 5) doses of methioninase are administered to the mammal, typically at different days, e.g. daily.

In an embodiment, an effective amount of the cofactor of methioninase is administered to the patient. It may be administered before, at the same time or after the administration of methioninase. In an embodiment it is present in the same composition than methioninase. In another embodiment, it is administered in a separate composition.

In an embodiment, administration of methioninase encapsulated into erythrocytes is performed, and cofactor may be encapsulated as well or the cofactor may be in free form in a solution. In a preferred embodiment, the cofactor is in solution in a pharmaceutically acceptable vehicle and is a non-phosphate form of vitamin B6, preferably PN. This solution of non-phosphate form of vitamin B6 may be administered by injection or oral route, or via any other route. In an embodiment, the solution is administered once or more after each injection of encapsulated methioninase, for example between 1 and 10 hours after. Preferably, the solution is administered advantageously once a day, or else twice or more per day, during the time of methioninase treatment or duration of methioninase activity in blood circulation (depending on the half-life thereof). With methioninase encapsulated inside erythrocytes, the cofactor in solution may be administered at least once a day during between 10 and 30 days.

In an embodiment, asparaginase under free form, pegylated form or encapsulated is administered once or more.

In another embodiment, free or pegylated asparaginase is administered more than once, for example two or more (e.g. 3, 4, 5) doses of asparaginase are administered to the mammal, typically at different days, e.g. daily.

In an embodiment, the methioninase and/or asparaginase is under powder form and the method of use comprises the solubilization thereof in a pharmaceutically acceptable solution or liquid before administering to the mammal.

In an embodiment, use is made of a device as described above. Thus the method of cancer treatment comprises the implantation or placing on the mammal, especially human, a device as described. The implantation or placing may comprise the connection of the tubes to a blood vessel or to a catheter and the like that is already in place. The method may then comprise starting the device for its sequential delivery according to a programming of its software in accordance with the method of the invention.

Advantageously, the suspension of erythrocytes encapsulating methioninase or asparaginase in preservation solution is ready to use, and preferably may have a low extracellular haemoglobin level, conforming in particular to FDA recommendations.

In a first embodiment, the injection is given to a mammal, especially a human patient of a suspension of RBCs encapsulating the active ingredient prepared between 1 and 72 h, in particular between 10 and 72 h before injection. The haematocrit of this suspension is 40% or higher. It is contained in a preservation solution. The extracellular haemoglobin level is 0.5 or lower, in particular 0.3 or lower, more particularly 0.2 or lower, preferably 0.15 or lower, further preferably 0.1 g/dl or lower, and/or the haemolysis rate is 2 or lower, in particular 1.5 or lower, preferably 1% or lower. The suspension is not subjected to washing or similar before injection.

In another embodiment, this method comprises the steps of providing packed red blood cells, placing it in suspension in physiological buffer at a haematocrit of 60 or 65% or higher, encapsulating the active ingredient in these RBCs using lysis and resealing procedure, incubating the RBCs obtained, washing the latter and collecting a final suspension of RBCs. The haematocrit of the suspension is 40% or higher. It is contained in a preservation solution. This suspension is stored at a temperature between 2 and 8° C. This final suspension is injected in the mammal, especially a human patient between 1 h and 72 h preferably between 24 and 72 h after preparation of the suspension. The extracellular haemoglobin level of this suspension is 0.5 or lower, in particular 0.3 or lower, more particularly 0.2 or lower, preferably 0.15 or lower, further preferably 0.1 g/dl or lower and/or its haemolysis rate is 2 or lower, in particular 1.5, or lower preferably 1% or lower. The suspension is not subjected to washing or similar before injection.

Compositions, kits and methods aim at treating liquid (hematologival) and solid tumors auxotrophic for asparagine and/or methioninase. As example leukemia (acute myeloid leukemia, acute promyelocytic leukemia) and gastric cancer (carcinoma stage IV, adenocarcinoma) may be cited.

The invention will now be described in further detail using the following non-limiting embodiments.

EXAMPLE 1

Figure 1:
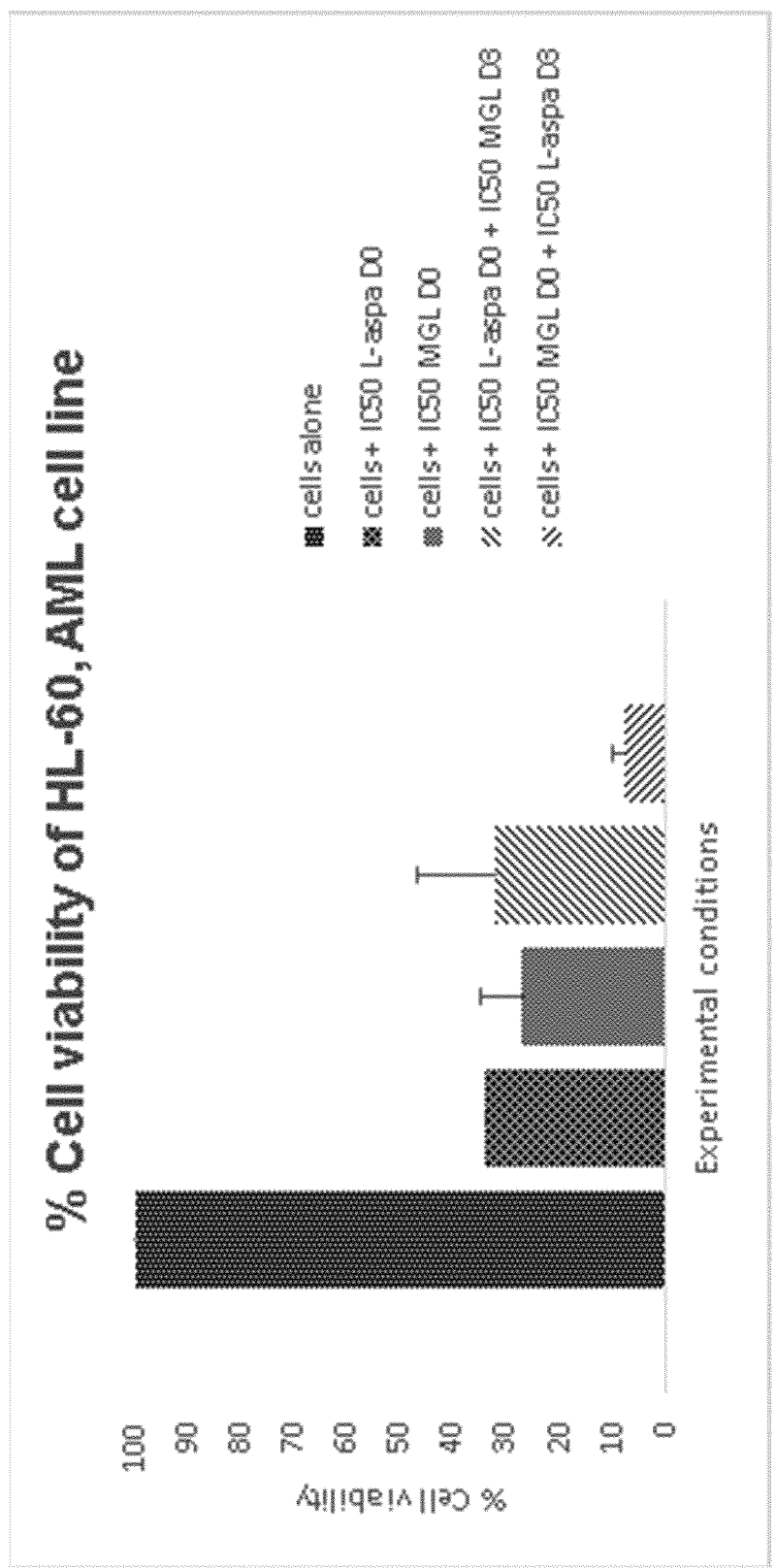
FIG. 1 is a graph showing % cell viability under different conditions of treatment.

I. Abbreviations
CCK-8: Cell counting kit-8
DPBS: Dulbecco's Phosphate-Buffered Saline
IMDM: Iscove's Modified Dulbecco's
MGL: Methionine-γ-lyase
v/v: Volume to volume
II. Operating Conditions
II.1 Test Item
  II.1.1. L-Asparaginase
Description: Medac® (Germany), E. coli L-asparaginase 10 000 IU
One concentration of L-asparaginase (2.53 IU/mL) was prepared by serial dilutions in Dulbecco Phosphate Buffered Saline (DPBS) 1×. Concentration of L-asparaginase was diluted 11-fold to obtain final concentration of 0.23 IU/mL (IC50).

II.1.2. Methionine-γ-Lyase (MGL)
Description: P. Putida methionine-γ-lyase (MGL) produced in E. coli.
One concentration of MGL (2.09 IU/mL) was prepared by serial dilutions in Dulbecco Phosphate Buffered Saline (DPBS) 1×. Concentration of MGL was diluted 11-fold to obtain final concentration of 0.19 IU/mL (IC50).
II.2 Cell Lines
  I.2.1. Description
Name: HL-60 cell line
Description: Human promyelocytic leukemia cell line (suspension)
Supplier and reference number: ATCC, CCL-240
  II.2.2. Culture Conditions
Cells were cultivated in a IMDM with L-glutamine medium and supplemented with 20% (v/v) of foetal bovine serum, 100 IU/mL of penicillin and 100 μg/mL of streptomycin. Subculturing was performed according to PO-CELL-002 and PO-CELL-005.
  II.2.3. Colorimetric Kit
Name: Cell Counting Kit-8 (CCK-8)
Supplier and reference number: Fluka 96992
Principle: the CCK-8 reagent contains a highly water-soluble tetrazolium salt WST-8. WST-8 is reduced by dehydrogenases in cells to give a yellow colored product (formazan) which is soluble in the tissue culture medium. The amount of the formazan dye generated by the activity of dehydrogenases in cells is directly proportional to the number of living cells.
The colorimetric test was performed according to PO-CELL-004.
III. Cytotoxicity Assay
III.1 Method
Fifteen thousand cells in 100 μL/well were dispensed in five 96-well flat bottom plates. In addition, 2 wells were filled with culture medium for blank control on each plate. All empty wells were filled with culture medium in order to minimize evaporation and condensation. On day 0 (D0), 10 μL of IC50 concentrations of L-asparaginase or MGL was added to the corresponding wells. Controls (blank wells and control plate) received 10 μL of DPBS 1×. On day 3 (D3), medium was removed from wells and replaced by fresh medium and 10 μL of DPBS 1× or 10 μL of IC50 concentrations of L-asparaginase (for cells previously incubated with MGL) or MGL (for cells previously incubated with L-asparaginase) added to the corresponding wells. Controls (blank and positive control) received 10 μL of DPBS 1×. Then, plates were incubated for 3 more days in the incubator. At the end of the incubation period (D6), 10 μL of CCK-8 solution were added to each well according to PO-CELL-004 and plates incubated for 2 hours in the incubator. Optical density (OD) was then determined at 450 nm using a microplate reader.
III.2 Internal Controls
Controls were performed in duplicate.
  III.2.1. Blank Wells
Slight spontaneous absorbance around 460 nm occurs in culture medium with CCK-8. This background absorbance depends on the culture medium, pH, incubation time and length of exposure to light. Therefore blank wells were performed containing 100 μL of culture medium and 10 μL of L-asparaginase or MGL diluent, DPBS 1×. The average absorbance of these control wells was subtracted to the others wells containing cells.

III.2.2. Viability Control (Positive Control)

As positive control for the HL-60 cell line (100% cell viability), cells were cultivated in the culture medium (100 µL) without L-asparaginase nor MGL, but with 10 µL of the diluent (DPBS 1×).

Determination of Cell Viability

Culture medium without cells constituted blank controls (OD Blank). Cells without L-asparaginase nor MGL constituted positive controls (viability control).

Percentage of living cells was calculated as shown below:

$$\frac{OD_{L\text{-}aspa+MGL^*} - OD_{Blank}}{OD_{viability\text{-}control^{**}} - OD_{Blank}} \times 100$$

*: cells with L-asparaginase and MGL treatment

Calculations were automatically performed via the Gen 5 software that pilots the microplate reader. The mean optical density (OD) of the 2 blank wells was automatically subtracted from all optical densities. Calculations of cell viability were realized for sequential treatment.

IV. Results

IV.1 Internal Control

Internal controls were acceptable, when it was not specified in raw data.

IV.2 IC50 Calculations with L-Asparaginase or MGL Alone

Percentages of cell viability with drug alone (MGL or L-asparaginase) were controlled in each experiment of drugs combination IV.2.1. Sequential Addition of L-Asparaginase and MGL The experiment with sequential treatment of L-asparaginase and MGL was done once with duplicate data. All quality controls (blank and positive control) were accepted in experiments. Details of % of cell viability calculations and graphical representation are presented below in table 1 and FIG. 1.

TABLE 1

% of cell viability for controls and enzyme association

| | % cell viability at D6 | |
|---|---|---|
| | Mean | SD |
| Cells alone | 100 | 25 |
| Cells + IC50 L-aspa D0 | 34 | 0 |
| Cells + IC50 MGL D0 | 27 | 8 |
| Cells + IC50 L-aspa D0 + IC50 MGL D3 | 32 | 15 |
| Cells + IC50 MGL D0 + IC50 L-aspa D3 | 8 | 2 |

Results indicated that enzyme association with MGL added at IC50 dose before the addition of L-asparaginase at IC50 dose (in red on FIG. 1) permitted to reduce cell viability of:

76% compared to IC50 L-asparaginase (IC50 control for L-asparaginase),

70% compared to MGL (IC50 control for MGL),

75% compared to enzyme association with L-asparaginase added in first at IC50 dose.

Yet, the reverse order of enzyme association did not give such results, with no benefits of the association on cell viability compared to enzymes alone (controls).

V. Conclusion

Sequential enzyme association demonstrated that cell mortality could be increased with an addition of MGL at IC50 dose followed 3 days later by the addition of L-asparaginase at IC50 dose. Yet, the reverse design of enzyme addition did not permit to obtain such results.

We can hypothesize that Met deprivation induced by MGL enzyme activity makes HL-60 leukemia cells more sensitive to L-asparaginase activity. Moreover, the roles of L-asparaginase and MGL have to be discussed considering their known respective effect. Indeed, L-asparaginase is known to trigger apoptosis in leukaemia cells (Ueno et al., 1997), therefore, it could probably plays a role of cytotoxic agent. MGL being known for blocking cell division in S or G2 phase of the cell cycle probably acts more as a cytostatic agent.

EXAMPLE 2: METHOD FOR ENCAPSULATION OF L-ASPARAGINASE IN MURINE ERYTHROCYTES

The L-asparaginase (Medac® E. coli L-asparaginase) is encapsulated in murine erythrocytes (OF1 mice) by the method of hypotonic dialysis in a dialysis bag. The blood is centrifuged beforehand to remove the plasma, and then washed three times with 0.9% NaCl. The haematocrit is adjusted to 70% in the presence of the asparaginase, added to a final concentration of 400 IU/ml of erythrocytes or red blood cells (RBC) before starting the dialysis. The dialysis lasts 50 minutes at 4° C. against a lysis buffer of low osmolarity. The murine erythrocytes are then resealed through the addition of a high osmolarity solution and incubating 30 minutes at 37° C. After two washings with 0.9% NaCl and one washing with Sag-mannitol supplemented with bovine serum albumin BSA (6%), the erythrocytes are adjusted to haematocrit 50%. The erythrocytes encapsulating the L-asparaginase are called L-Aspa RBC. The encapsulation generates L-Aspa RBC at a concentration of 40 IU of asparaginase/ml of RC at 50% haematocrit.

During the encapsulation procedure, the whole blood, the washed RBC, the RBC mixed with the L-asparaginase (before dialysis) and the RBC loaded with L-asparaginase (after dialysis) are tested for:

haematocrit (Ht)
average corpuscular volume (ACV)
average corpuscular haemoglobin concentration (ACHC)
total haemoglobin concentration and
cell count.

Aliquots of the cell suspensions are withdrawn before and after the hypotonic dialysis for measurement of the L-asparaginase enzyme activity. The estimation of the L-asparaginase was performed according to the protocol published in: Orsonneau et al., Ann Biol Clin, 62: 568-572.

EXAMPLE 3: ENCAPSULATION OF L-ASPARAGINASE IN HUMAN ERYTHROCYTES

The method described in WO-A-2006/016247 is used to produce a batch of erythrocytes encapsulating L-asparaginase. In accordance with the teaching of WO-A-2006/016247, the osmotic fragility is considered and the lysis parameters are adjusted accordingly. (flow rate of the erythrocyte suspension in the dialysis cartridge is adjusted). The method is further performed in conformity with the physician prescription, which takes into account the weight of the patient and the dose of L-asparaginase to be administered. The specifications of the end product are as follows:
- mean corpuscular volume (MCV): 70-95 fL
- mean corpuscular haemoglobin concentration (MCHC): 23-35 g/dL
- extracellular haemoglobin ≤0.2 g/dL of suspension
- osmotic fragility ≤6 g/L of NaCl
- mean corpuscular L-asparaginase concentration: 78-146 IU/mL
- extracellular L-asparaginase ≤2% of the total enzyme activity.

The suspension of erythrocytes so obtained is called GRASPA® and is mentioned in the literature.

EXAMPLE 4. METHOD FOR OBTAINING AND CHARACTERIZING METHIONINE GAMMA LYASE (MGL)

Production of the strain and isolation of a hyper-producing clone: the natural sequence of MGL of *Pseudomonas putida* (GenBank: D88554.1) was optimized by modifying rare codons (in order to adapt the sequence stemming from *P. putida* to the production strain *Escherichia coli*). Other changes have been made to improve the context of translation initiation. Finally, silent mutations were performed to remove three elements that are part of a putative bacterial promoter in the coding sequence (box −35, box −10 and a binding site of a transcription factor in position 56). The production strain *E. coli* HMS174 (DE3) was transformed with the expression vector pGTPc502_MGL (promoter T7) containing the optimized sequence and a producing clone was selected. The producing clone is pre-cultivated in a GY medium+0.5% glucose+kanamycin for 6-8 h (pre-culture 1) and 16 h (pre-culture 2) at 37° C.

Fermentation: the production is then achieved in a fermenter with GY medium, with stirring, controlled pressure and pH from the pre-culture 2 at an optical density of 0.02. The growth phase (at 37° C.) takes place until an optical density of 10 is obtained and the expression induction is achieved at 28° C. by adding 1 mM IPTG into the culture medium. the cell sediment is harvested 20 h after induction in two phases: the cell broth is concentrated 5-10 times after passing over a 500 kDa hollow fiber and then cell pellet is recovered by centrifugation at 15900×g and then stored at −20° C.

Purification: The cell pellet is thawed and suspended in lysis buffer (7 v/w). Lysis is performed at 10° C. in three steps by high pressure homogenization (one step at 1000 bars, and then two steps at 600 bars). The cell lysate then undergoes clarification at 10° C. by adding 0.2% PEI and centrifugation at 15900×g. The soluble fraction is then sterilized by 0.2 µm before precipitation with ammonium sulfate (60% saturation) at 6° C., over 20 h. Two crystallization steps are carried out on the re-solubilized sediment using solubilization buffer, the first crystallization step is realized by addition of PEG-6000 at 10% (final concentration) and ammonium sulfate at 10% saturation, and the second crystallization is then performed by addition of PEG-6000 at 12% final concentration and 0.2M NaCl (final concentration) at 30° C. The pellets containing the MGL protein are harvested at each stage after centrifugation at 15900×g. The pellet containing the MGL protein is re-suspended in a solubilization buffer and passed over a 0.45 µm filter before being subject to two anion exchange chromatographies (DEAE sepharose FF). The purified protein is then subject to a polishing step and passed over a Q membrane chromatography capsule for removing the different contaminants (endotoxins, HCP host cell protein, residual DNA). Finally, the purified MGL protein is concentrated at 40 mg/ml and diafiltered in formulation buffer using a 10 kDa cut-off tangential flow filtration cassette. Substance is then aliquoted at ~50 mg of protein per vial, eventually freeze-dried under controlled pressure and temperature, and stored at −80° C.

Characterization: The specific activity of the enzyme is determined by measuring the produced $NH_3$ as described in WO 2015/121348. The purity is determined by SDS-PAGE. The PLP level after being taken up in water was evaluated according to the method described in WO 2015/121348. The osmolarity is measured with an osmometer (Micro-Osmometer Loser Type 15).

The following table 2 summarizes the main characteristics of one produced batch of MGL:

| | MGL of *P. putida* |
|---|---|
| Formulation | Freeze-dried (amount per tube: 49.2 mg). Characteristics after being taken up in 625 µL of water: 78.7 mg/ml, ~622 µM of PLP, 50 mM of Na phosphate, pH 7.2, Osmolarity 300 mOsmol/kg. |
| Specific activity | 13.2 IU/mg |
| Purity | >98% |

Discussion of the production method. The method for purifying the MGL described in in WO 2015/121348 is established on the basis of the method detailed in patent EP 978 560 B1 and of the associated publication (Takakura et al., Appl Microbiol Biotechnol 2006). This selection is explained by the simplicity and the robustness of the crystallization step which is described as being particularly practical and easily adaptable to large scale productions according to the authors. This step is based on the use of PEG6000 and of ammonium sulfate after heating the MGL solution obtained after the lysis/clarification and removal of impurities by adding PEG6000/ammonium sulfate steps. The other notable point of this step is the possibility of rapidly obtaining a high purity level during the step for removing the impurities by achieving centrifugation following the treatment of the MGL solution with PEG6000. The impurities are again found in the centrifugation pellet, the MGL being in majority found in solution in the supernatant. Because of this purity, the passing of the MGL solution in a single chromatography step over an anion exchanger column (DEAE), associated with a purification step by gel filtration on a sephacryl S200 HR column, gives the possibility of obtaining a purified protein.

Upon setting into place the patented method for small scale tests, it appeared that the obtained results were not able to be reproduced. According to patent EP 0 978 560 B1, at the end of the step for removing the impurities (treatment with PEG6000/ammonium sulfate and centrifugation), the MGL enzyme is in majority found in the soluble fraction, centrifugation causing removal of the impurities in the pellet. During small scale tests conducted according to the described method in EP 0 978 560 B1, the MGL protein is again in majority found (~80%) in the centrifugation pellet. The table 3 below lists the percentage of MGL evaluated by densitometry on SDS-PAGE gel in soluble fractions.

| Purification | MGL percentage in the soluble fraction | Average |
|---|---|---|
| Test no. 1 | 11% | 17% |
| Test no. 2 | 23% | |

This unexpected result therefore led to optimization of the patented method by: 1) operating from the centrifugation pellet containing MGL, 2) carrying out two successive crystallization steps for improving the removal of the impurities after loading on a DEAE column, 3) optimizing chromatography on a DEAE column.

For this last step, it is found that the DEAE sepharose FF resin is finally not a sufficiently strong exchanger in the tested buffer and pH conditions. After different additional optimization tests, the selection was finally directed to 1) replacement of the phosphate buffer used in the initial method with Tris buffer pH 7.6 for improving the robustness of the method and 2) carrying out a second passage on DEAE in order to substantially improve the endotoxin level and the protein purity without any loss of MGL (0.8 EU/mg according to Takakura et al., 2006 versus 0.57 EU/mg for the modified method).

Finally, in order to obtain a method compatible with the requirements for large scale GMP production, a polishing step on a membrane Q was added in order to reduce the residual endotoxins and HCP levels. This final step of polishing avoids the implementation of the S200 gel filtration chromatography which is a difficult step to be used in production processes at an industrial scale (cost and duration of the chromatography).

Product obtained is summarized in the following table 4 using the two methods.

| | Patent EP 978 560 B1 | | Method of the application | |
|---|---|---|---|---|
| Step | Amount of enzyme (g) | Yield (%) | Amount of enzyme (g) | Yield (%) |
| Solubilised pellet before DEAE | 125 | 100 | 70 | 100 |
| Concentrated solution$ | 80 | 64 | 46 | 65 |

$post sephacryl S-200 HR (EP 978 560) or post Membrane Q (method of the invention).

EXAMPLE 5. CO-ENCAPSULATION OF MGL AND PLP IN MURINE ERYTHROCYTES

Whole blood of CD1 mice (Charles River) is centrifuged at 1000×g, for 10 min, at 4° C. in order to remove the plasma and buffy coat. The RCs are washed three times with 0.9% NaCl (v:v). The freeze-dried MGL is re-suspended in water at a concentration of 78.7 mg/ml and added to the erythrocyte suspension in order to obtain a final suspension with a hematocrit of 70%, containing different concentrations of MGL and of the PLP. The suspension was then loaded on a hemodialyzer at a flow rate of 120 ml/h and dialyzed against a hypotonic solution at a flow rate of 15 ml/min as a counter-current. The suspension was then resealed with a hypertonic solution and then incubated for 30 min at 37° C. After three washes in 0.9% NaCl, 0.2% glucose, the suspension was taken up in a preservation solution SAG-Mannitol supplemented with 6% BSA. The obtained products are characterized at D0 (within the 2 h following their preparation) and at D1 (i.e. after ~18 h-24 h of preservation at 2-8° C.). The hematologic characteristics are obtained with a veterinary automaton (Sysmex, PocH-100iV).

Results:

In the different studies mentioned hereafter, the MGL activity in the finished products is assayed with the method described in example 5 against an external calibration range of MGL in aqueous solution. These results, combined with explanatory studies, show that MGL activity in the finished products increases with the amount of enzyme introduced into the method and that it is easily possible to encapsulate up to 32 IU of MGL per ml of finished product while maintaining good stability.

In another study, three murine finished products RC-MGL-PLP1, RC-MGL-PLP2 and RC-MGL-PLP3 were prepared according to the following methods:

RC-MGL-PLP1: co-encapsulation of MGL and of PLP from a suspension containing 3 mg/ml of MGL and ~30 µM of PLP. The final product was taken up in SAG-Mannitol, 6% BSA supplemented with final 10 µM PLP.

RC-MGL-PLP2: co-encapsulation of MGL and of PLP from a suspension containing 3 mg/ml of MGL and ~30 µM of PLP. The finished product was taken up in SAG-Mannitol 6% BSA.

RC-MGL-PLP3: this product stems from a co-encapsulation of MGL and PLP from a suspension containing 3 mg/ml of MGL and ~124 µM of PLP. The final product was taken up in SAG-Mannitol 6% BSA.

In a third study, a murine finished product RC-MGL-PLP4 was prepared from a new batch of MGL according to the following methods:

RC-MGL-PLP4: co-encapsulation of MGL and the PLP from a suspension containing 5 mg/ml of MGL and ~35 µM of PLP. The finished product was taken up in SAG-Mannitol 6% BSA.

Finally in a fourth study, a murine product RC-MGL-PLP5 was prepared from a third batch of MGL according to the following methods:

RC-MGL-PLP5: co-encapsulation of MGL and PLP from a suspension containing 6 mg/ml of MGL and ~100 µM of PLP. The finished product was taken up in SAG-Mannitol 6% BSA.

The hematologic and biochemical characteristics of the three finished products at D0 (after their preparation) are detailed in the table 5 below. The encapsulation yields are satisfactory and vary from 18.6% to 30.5%.

| | | RC-MGL-PLP1 | RC-MGL-PLP2 | RC-MGL-PLP3 | RC-MGL-PLP4 | RC-MGL-PLP5 |
|---|---|---|---|---|---|---|
| Hematological data | Hematocrit (%) | 50.0 | 49.6 | 50.0 | 50.0 | 50.0 |
| | Corpuscle volume (fl) | 46.3 | 46.5 | 46.8 | 42.4 | 45.6 |
| | Corpuscle hemoglobin (g/dl) | 24.7 | 24.0 | 24.2 | 27.4 | 25.1 |
| | RC concentration ($10^6$/µl) | 6.5 | 6.9 | 6.6 | 7.2 | 6.0 |
| | Total hemoglobin (g/dl) | 14.8 | 15.4 | 15.0 | 16.6 | 13.8 |
| | Extracellular Hb (g/dl) | 0.1 | 0.1 | 0.1 | 0.2 | 0.05 |

-continued

|  |  | RC-MGL-PLP1 | RC-MGL-PLP2 | RC-MGL-PLP3 | RC-MGL-PLP4 | RC-MGL-PLP5 |
|---|---|---|---|---|---|---|
| mgl | Intra-erythrocyte concentration of MGL (mg/ml of RC) | 0.97 | 0.94 | 0.79 | 1.01 | 1.36 |
|  | Intra-erythrocyte activity of MGL (IU/ml of RC)* | 12.8 | 12.4 | 8.8 | 5.0 | 8.6 |
|  | Extracellular activity (%) | 0.92% | 0.97% | 1.32% | 1.18% | 2.23% |
|  | Intracellular activity (%) | 99.08% | 99.03% | 98.68% | 98.82% | 97.77% |
|  | Encapsulation yield of MGL (%) | 18.6% | 30.5% | 22.6% | 19.4% | 22.7% |
| PLP | Intra-erythrocyte concentration of PLP (μmol/l of RC) | ND | 13.4 | 71.4 | 10.2 | ND |
|  | Intracellular PLP fraction (%) | ND | 99.5 | 98.7 | 98.1 | ND |
|  | Extracellular PLP fraction (%) | ND | 0.5 | 1.3 | 1.92 | ND |
|  | PLP encapsulation yield (%) | ND | 44.8 | 57.4 | 30.7 | ND |

*Calculated from the specific activity of each batch.

EXAMPLE 6. PRODUCTION OF HUMAN RCS ENCAPSULATING METHIONINE GAMMA LYASE AND PLP ACCORDING TO THE INDUSTRIAL METHOD

A pouch of leukocyte-depleted human Red Cell RCs (provided by the "Etablissement Francais du Sang") is subject to a cycle of three washes with 0.9% NaCl (washer Cobe 2991). The freeze-dried MGL is re-suspended with 0.7% NaCl and added to the erythrocyte suspension in order to obtain a final suspension with a hematocrit of 70%, containing 3 mg/ml of MGL and ~30 μM of PLP (stemming from the formulation of MGL). The suspension is homogenized and it is proceeded with encapsulation according to the method described in EP 1 773 452. The suspension from the resealing is then incubated for 3 h at room temperature in order to remove the most fragile RCs. The suspension is washed three times with a 0.9% NaCl, 0.2% glucose solution (washer Cobe 2991) and then re-suspended with 80 ml of preservation solution (AS-3). The encapsulated MGL level is assayed like in Example 6, see table 6 below.

|  | J0 | J1 | J7 |
|---|---|---|---|
| Hematocrit (%) | 52.0 | 51.6 | 52.7 |
| Corpuscle volume (fl) | 91.0 | 92.0 | 88.0 |
| Corpuscle hemoglobin (g/dl) | 30.3 | 29.8 | 31.6 |
| RC concentration ($10^6/\mu l$) | 6.00 | 5.92 | 5.98 |
| Total hemoglobin (g/dl) | 16.4 | 16.2 | 16.6 |
| Extracellular Hb (g/dl) | 0.119 | 0.197 | 0.280 |
| Osmotic fragility (g/l) | 1.17 |  |  |
| Hemolysis (%) | 0.7% | 1.2% | 1.7% |
| Total MGL concentration (mg/ml) | 0.36 | 0.35 |  |
| MGL supernatant concentration (mg/ml) | 0.01 | 0.01 |  |
| MGL intra-erythrocyte concentration (mg/ml, 100% Ht) | 0.68 | 0.67 |  |
| Extracellular activity (%) | 1.3% | 1.4% |  |
| Intracellular activity (%) | 98.7% | 98.6% |  |
| Encapsulation yield (%) | 19.7% |  |  |

EXAMPLE 7

Additional Abbreviations
RPMI: Le Roswell park memorial institute medium
I. Operating Conditions
  I.1 Test Item
    I.1.1. L-Asparaginase
Description: Medac® (Germany), E. coli L-asparaginase 10 000 IU.
One concentration of L-asparaginase (2.2 IU/mL) was prepared by serial dilutions in Dulbecco Phosphate Buffered Saline (DPBS) 1×. Concentration of L-asparaginase was diluted 11-fold to obtain final concentration of 0.20 IU/mL (IC50).
    I.1.2. Methionine-γ-Lyase (MGL)
Description: P. Putida methionine-γ-lyase (MGL) produced in E. Coll.
One concentration of MGL (3.85 IU/mL) was prepared by serial dilutions in Dulbecco Phosphate Buffered Saline (DPBS) 1×. Concentration of MGL was diluted 11-fold to obtain final concentration of 0.35 IU/mL (IC50).
  I.2 Cell Lines
    I.2.1. Description
Name: NCI-N87 cell line
Description: Human gastric carcinoma cell line (adherent)
Supplier and reference number: ATCC, CRL-5822
    I.2.2. Culture Conditions
Cells were cultivated in a RPMI media supplemented with 10% (v/v) of foetal bovine serum, 100 IU/mL of penicillin and 100 μg/mL of streptomycin. Subculturing was performed according to PO-CELL-002 and PO-CELL-005.
    I.2.3. Colorimetric Kit
Name: Cell Counting Kit-8 (CCK-8)
Supplier and reference number: Fluka 96992
Principle: the CCK-8 reagent contains a highly water-soluble tetrazolium salt WST-8. WST-8 is reduced by dehydrogenases in cells to give a yellow colored product (formazan) which is soluble in the tissue culture medium. The amount of the formazan dye generated by the activity of dehydrogenases in cells is directly proportional to the number of living cells. The colorimetric test was performed according to PO-CELL-004.
II. Cytotoxicity Assay
  II.1 Method
Two thousand five hundred cells in 100 μL/well were dispensed in 96-well flat bottom plates (cf. number of plates in raw data). In addition, two wells were filled with culture medium for blank control on each plate. All empty wells were filled with culture medium in order to minimize evaporation and condensation. On day 0 (D0), 10 μL of IC50 concentrations of L-asparaginase or MGL were added to the corresponding wells. Controls (blank wells and control plate) received 10 μL of DPBS 1×. On day 4 (D4), medium was removed from wells and replaced by fresh medium and 10 μL of DPBS 1× or 10 μL of IC50 concentrations of L-asparaginase (for cells previously incubated with MGL) or MGL (for cells previously incubated with L-asparaginase) added to the corresponding wells. Controls (blank and positive control) received 10 μL of DPBS 1x. Then, plates were incubated for 4 more days in the incubator. At the end of the incubation period (D8), 10 μL of CCK-8 solution were added to each well according to PO-CELL-004 and plates incubated for 4 hours. Optical density (OD) was then determined at 450 nm using a microplate reader.

II.2 Internal Controls

Controls were performed in duplicate.

II.2.1. Blank Wells

As above in Example 1.

II.2.2. Viability Control (Positive Control)

As positive control for the NCI-N87 cell line (100% cell viability), cells were cultivated in the culture medium (1.00 μL) without L-asparaginase nor MGL, but with 10 μL of the diluent (DPBS 1x).

II.3 Determination of Cell Viability

As above in Example 1.

III. Results

III.1 Internal Control

Internal controls were acceptable when it was not specified in raw data.

III.2 IC50 Calculations with L-Asparaginase or MGL Alone

Percentages of cell viability with drug alone (MGL or L-asparaginase) were controlled in each experiment of drugs combination. Fifty percent of cell viability are expected at half of the test (D4) because IC50 value used here for enzymes were previously validated in single treatment at D4.

III.2.1. Sequential Addition of L-Asparaginase and MGL

The experiment with sequential treatment of L-asparaginase and MGL was done twice with duplicate data. All quality controls (blank and positive control) were accepted in experiments.

Figure 2:
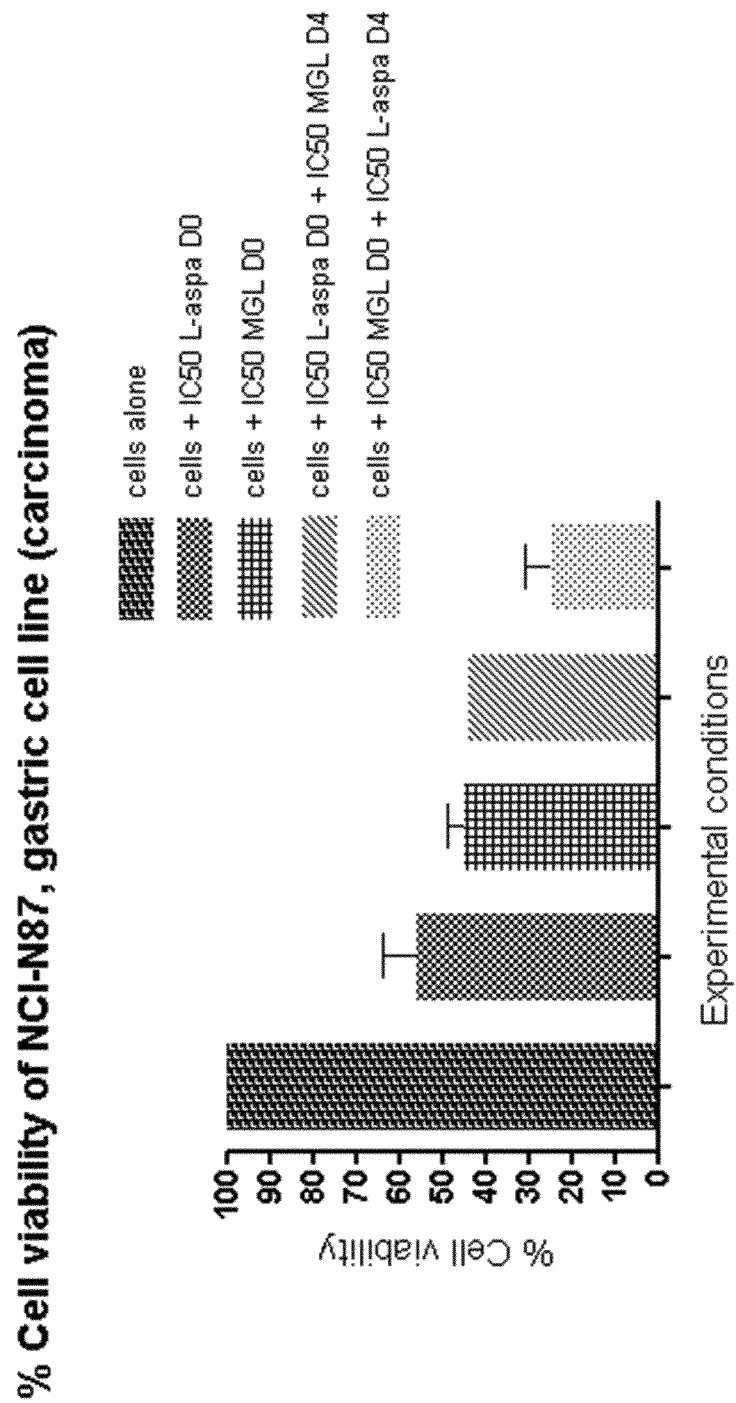
FIGS. 2 and 3 are graphs showing % cell viability under different conditions of treatment.

Details of % of cell viability calculations and graphical representation are presented below in table 7 and FIG. 2.

TABLE 7

% of cell viability for controls and enzyme association

| | % cell viability at D8 | |
|---|---|---|
| | Mean | SD |
| Cells alone | 100 | 0 |
| Cells + IC50 L-aspa D0 | 56 | 8 |
| Cells + IC50 MGL D0 | 45 | 4 |
| Cells + IC50 L-aspa D0 + IC50 MGL D3 | 44 | 0 |
| Cells + IC50 MGL D0 + IC50 L-aspa D3 | 25 | 6 |

Results indicated that enzyme association with MGL added at IC50 dose before the addition of L-asparaginase at IC50 dose (cf. FIG. 2) permitted to reduce cell viability of:
- 55% compared to 1050 L-asparaginase (IC50 control for L-asparaginase),
- 44% compared to MGL (1050 control for MGL),
- 43% compared to enzyme association with L-asparaginase added in first at IC50 dose.

IV. Conclusion

Sequential enzyme association demonstrated that cell mortality could be increased with an addition of MGL at IC50 dose followed 4 days later by the addition of L-asparaginase at IC50 dose.

We can hypothesize that Met deprivation induced by MGL enzyme activity makes NCI-N87 gastric cells more sensitive to L-asparaginase activity. Moreover, the roles of L-asparaginase and MGL have to be discussed considering their known respective effect. Indeed, L-asparaginase is known to trigger apoptosis in leukaemia cells (Ueno et al., 1997), therefore, it could probably plays a role of cytotoxic agent. MGL being known for blocking cell division in S or G2 phase of the cell cycle probably acts more as a cytostatic agent.

EXAMPLE 8

I. Additional Abbreviations

F12K: Kaighn's modification of ham's F-12

II. Operating Conditions

II.1 Test Item

II.1.1. L-Asparaginase

Description: Medac® (Germany), E. Coli L-asparaginase 10 000 IU.

One concentration of L-asparaginase (2.97 IU/mL) was prepared by serial dilutions in Dulbecco Phosphate Buffered Saline (DPBS) 1x. Concentration of L-asparaginase was diluted 11-fold to obtain final concentration of 0.27 IU/mL (IC50).

II.1.2. Methionine-γ-Lyase (MGL)

Description: P. Putida methionine-γ-lyase (MGL) produced in E. Coli.

One concentration of MGL (1.43 IU/mL) was prepared by serial dilutions in Dulbecco Phosphate Buffered Saline (DPBS) 1x. Concentration of MGL was diluted 11-fold to obtain final concentration of 0.13 IU/mL (1050).

II.2 Cell Lines

II.2.1. Description

Name: AGS cell line

Description: Human gastric adenocarcinoma cell line (adherent)

Supplier and reference number: ATCC, CRL-1739

II.2.2. Culture Conditions

Cells were cultivated in a F12K media with L-glutamine supplemented with 10% (v/v) of foetal bovine serum, 100 IU/mL of penicillin and 100 μg/mL of streptomycin. Subculturing was performed according to PO-CELL-002 and PO-CELL-005.

II.2.3. Colorimetric Kit

Name: Cell Counting Kit-8 (CCK-8)

Supplier and reference number: Fluka 96992

Principle: the CCK-8 reagent contains a highly water-soluble tetrazolium salt WST-8. WST-8 is reduced by dehydrogenases in cells to give a yellow colored product (formazan) which is soluble in the tissue culture medium. The amount of the formazan dye generated by the activity of dehydrogenases in cells is directly proportional to the number of living cells. The colorimetric test was performed according to PO-CELL-004.

III. Cytotoxicity Assay

III.1 Method

One thousand cells in 100 μL/well were dispensed in 96-well flat bottom plates (cf. number of plates in raw data). In addition, two wells were filled with culture medium for blank control on each plate. All empty wells were filled with culture medium in order to minimize evaporation and condensation. On day 0 (D0), 10 μL of IC50 concentrations of L-asparaginase or MGL were added to the corresponding wells. Controls (blank wells and control plate) received 10 μL of DPBS 1x. On day 4 (D4), medium was removed from wells and replaced by fresh medium and 10 μL of DPBS 1x or 10 μL of IC50 concentrations of L-asparaginase (for cells previously incubated with MGL) or MGL (for cells previously incubated with L-asparaginase) added to the corresponding wells. Controls (blank and positive control) received 10 μL of DPBS 1×. Then, plates were incubated for 4 more days in the incubator. At the end of the incubation period (D8), 10 μL of CCK-8 solution were added to each well according to PO-CELL-004 and plates incubated for 4 hours. Optical density (OD) was then determined at 450 nm using a microplate reader.

III.2 Internal controls

Controls were performed in duplicate.

III.2.1. Blank Wells

As above in Example 1.

III.2.2. Viability Control (Positive Control)

As positive control for the AGS cell line (100% cell viability), cells were cultivated in the culture medium (100 μL) without L-asparaginase nor MGL, but with 10 μL of the diluent (DPBS 1×).

III.3 Determination of Cell Viability

As above in Example 1.

IV. Results

IV.1 Internal Control

Internal controls were acceptable when it was not specified in raw data.

IV.2 IC50 calculations with L-asparaginase or MGL alone

Percentages of cell viability with drug alone (MGL or L-asparaginase) were controlled in each experiment of drugs combination. Fifty percent of cell viability are expected at half of the test (D4) because IC50 value used here for enzymes were previously validated in single treatment at D4.

IV.2.1. Sequential Addition of L-Asparaginase and MGL

The experiment with sequential treatment of L-asparaginase and MGL was done twice with duplicate data. All quality controls (blank and positive control) were accepted in experiments.

Figure 3:
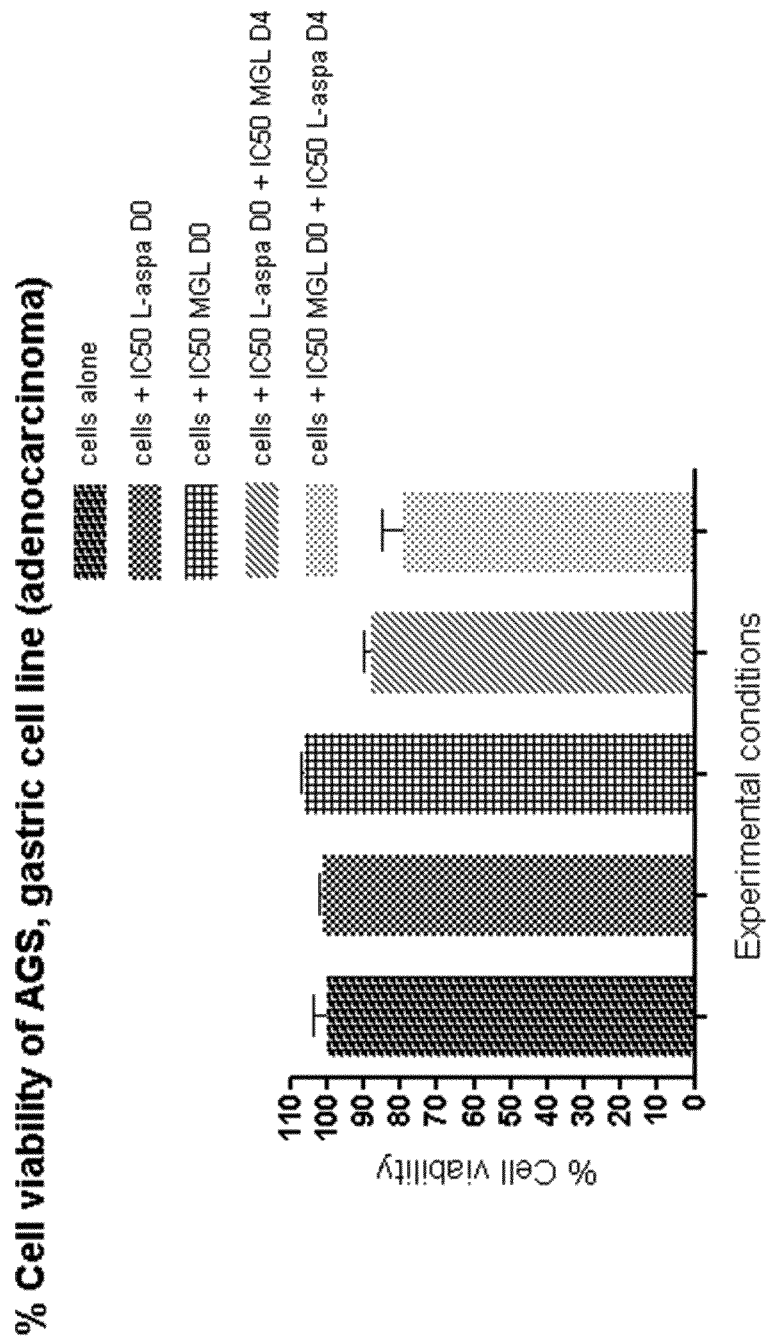

Details of % of cell viability calculations and graphical representation are presented below in table 8 and FIG. 3.

TABLE 8

% of cell viability for controls and enzyme association

| | % cell viability at D8 | |
|---|---|---|
| | Mean | SD |
| Cells alone | 100 | 4 |
| Cells + IC50 L-aspa D0 | 101 | 1 |
| Cells + IC50 MGL D0 | 106 | 1 |
| Cells + IC50 L-aspa D0 + IC50 MGL D3 | 88 | 2 |
| Cells + IC50 MGL D0 + IC50 L-aspa D3 | 79 | 6 |

Results indicated that enzyme association with MGL added at IC50 dose before the addition of L-asparaginase at IC50 dose (cf. FIG. 3) permitted to reduce cell viability of:
- 22% compared to IC50 L-asparaginase (IC50 control for L-asparaginase),
- 26% compared to MGL (IC50 control for MGL),
- 10% compared to enzyme association with L-asparaginase added in first at IC50 dose.

Moreover, for precision here, IC50 control for L-asparaginase or MGL (used and validated initially at D4) returned to 100% of cell viability after 8 days of culture with renewal of media at D4/half of the test. Indeed, remaining viable cells at D4 could re-growth with addition of "fresh" nutrients. Results were conform for IC50 controls (enzyme alone) reaching 50% of cell viability at D4.

V. Conclusion

Sequential enzyme association demonstrated that cell mortality could be increased with an addition of MGL at IC50 dose followed 4 days later by the addition of L-asparaginase at IC50 dose.

We can hypothesize that Met deprivation induced by MGL enzyme activity makes AGS gastric cells more sensitive to L-asparaginase activity. Moreover, the roles of L-asparaginase and MGL have to be discussed considering their known respective effect. Indeed, L-asparaginase is known to trigger apoptosis in leukaemia cells (Ueno et al., 1997), therefore, it could probably plays a role of cytotoxic agent. MGL being known for blocking cell division in S or G2 phase of the cell cycle probably acts more as a cytostatic agent.

EXAMPLE 9

I. Additional Abbreviations

A.M.: Ante meridiem
ERY-ASP: L-asparaginase encapsulated into red blood cells
ERY-MET: Methionine gamma-lyase encapsulated into red blood cells
IG: Intragastric injection (gavage)
IU: International Unit corresponding to μmol/min
IV: Intravenous
ND: Not determined
PN: Pyridoxine
TGI: Tumor growth inhibition II. Objective of In Vivo Study The objective of this study is to determine if combination of methioninase-loaded erythrocytes (ERY-MET) with L-asparaginase-loaded erythrocytes (ERY-ASP) can improve the antitumor activity observed with ERY-MET alone in a NCI-N87 gastric tumor subcutaneous xenograft mouse model.

III. Operating Conditions

NCI-N87 cells were cultivated at ERYTECH Pharma and prepared at $5.10^7$ cells/mL in DPBS 1× for injection. Four groups of 10 or 12 female NMRI nude mice (groups 1, 2, 3 and 4) were subcutaneously injected with the cell line at the fixed concentration of $5.10^6$/100 μL. ERY-MET and ERY-ASP injections were administrated (I.V. route) respectively at 108 IU/kg (8 mL/kg) and 200 IU/kg (4-5.4 mL/kg). Group 2 received 3 injections of ERY-MET on days 7, 14 and 21. Group 3 (ERY-ASP/ERY-MET) received 1 injection of ERY-ASP on day 7 and then, 2 injections of ERY-MET on days 21 and 28. Group 4 (ERY-MET/ERY-ASP) received 2 injections of ERY-MET on days 7 and 14 and then 1 injection of ERY-ASP on day 21. Group 1 was administered with the preservative solution of ERY-MET (SAG mannitol/plasma) at 8 mL/kg on days 7, 14 and 21.

Oral administrations (gavage) of PN co-factor was performed 6 hours after each ERY-MET injection (Day 7+6 h, Day 15+6 h, Day 21+6 h for group 2; Day 21+6 h, Day 28+6 h for group 3; Day 7+6 h, Day 15+6 h for group 4) and once a day (A.M.) for the other days (without ERY-MET administration) until Day 20 (for group 4), Day 27 (for group 2) or Day 34 (for group 3).

IV. Results

Tumor volume regression associated to ERY-MET/ERY-ASP combination appeared different to this observed for ERY-MET arm; indeed at D37, mice ERY-MET displayed a mean tumor volume of 298.3±36.2 mm³ and mice ERY-MET/ERY-ASP displayed a mean tumor volume of 189.7±29.8 mm³ corresponding to respectively 37% and 57% of mean tumor volume reduction while mice given vehicle (control) had a mean tumor volume of 441.5±56.6 mm³. Percentage of tumor growth inhibition (TGI*) were calculated for the enzyme association ERY-MET/ERY-ASP vs control (vehicle group) or vs ERY-MET group according to the following formula:

$$100 - \left( \frac{\text{Tumor } Volume_{enzyme\ association}\ \text{at Day } X}{\text{Tumor } Volume_{vehicle\ or\ ERY\text{-}MET\ alone}\ \text{at Day } X} \right)$$

Results are presented below in the table 9 below:

TABLE 9

| TGI calculations for the association ERY-MET/ERY-ASP | | |
|---|---|---|
| % TGI for ERY-MET/ERY-ASP treatment | vs control | vs ERY-MET alone |
| Day 7 | ND** | ND** |
| Day 20 | 41% | 33% |
| Day 37 | 57% | 36% |

**Not determined (not relevant) due to low volume measure disparity at the beginning of the study (D7 is the first time point of tumor volume measure).

Figure 4:
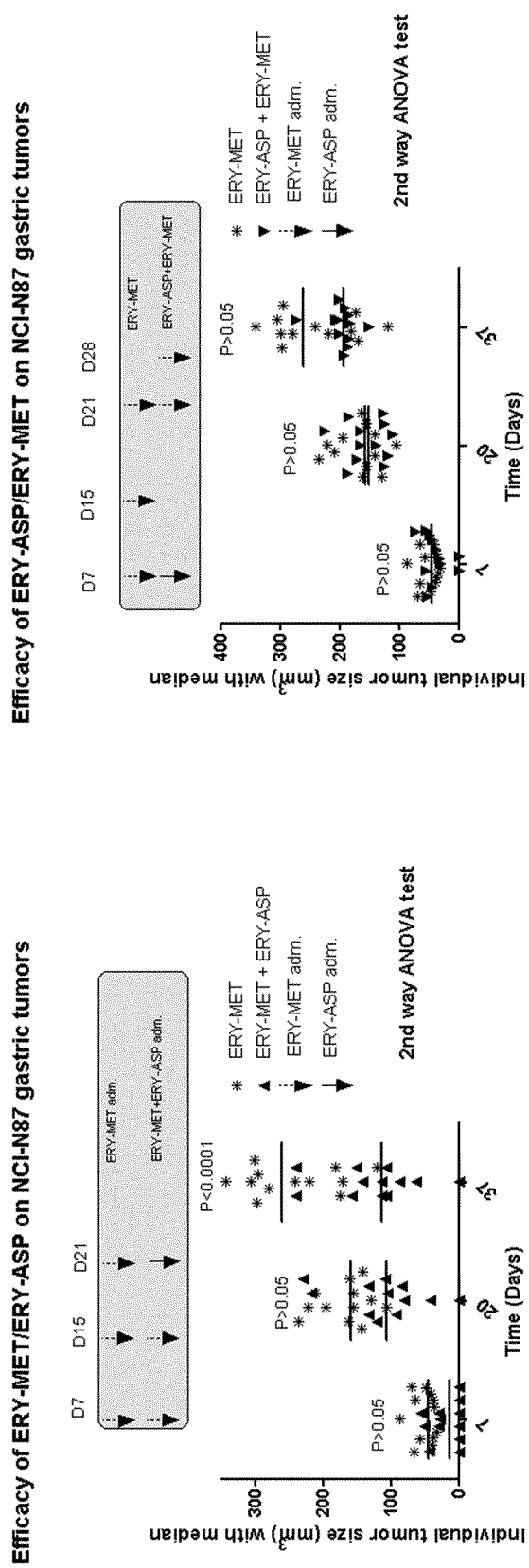
FIG. 4 is a graph showing individual tumor volume with median in function of time.

In order to assess significance between groups and efficiency of ERY-MET/ERY-ASP treatment compared to ERY-MET alone on NCI-N87 gastric tumors, a two-way ANOVA test was performed with GraphPad Prism software (version 5.04) on tumor growth measures. Analysis comparing vehicle (control), ERY-MET and ERY-MET/ERY-ASP treatment indicating significance between groups at D37 with a P value inferior to 0.0001 (cf. FIG. 4) revealing efficacy of the combination ERY-MET/ERY-ASP 16 days after last injections for treatment against gastric tumors. With the reverse scheme of administration ERY-ASP/ERY-MET treatment compared to ERY-MET alone on NCI-N87 gastric tumors, two-way ANOVA test (cf. FIG. 4) revealed no significance between groups for three time points of follow-up (D7/D20/D37) with a P value >0.05.

V. Conclusion

ERY-MET was combined to ERY-ASP with 2 scheme of administrations: 1-ERY-ASP (D7)-ERY-MET (D21/D28) and 2-ERY-MET (D7/D15)-ERY-ASP (D21). Positive response compared to ERY-MET alone seems to appear when ERY-MET was administrated (twice) before ERY-ASP. This significance of result is supported by the obtaining of a P value inferior to 0.0001 at D37 on individual tumor volume measure.

The invention claimed is:

1. A method for treating cancer in a mammal in need thereof, the method comprising administering to the mammal in need thereof, a composition comprising a methioninase and then a composition containing an asparaginase, wherein there is a delay of between about 1 h and about 30 days between the end of the methioninase administration and the initiation of the asparaginase administration, and wherein:
   when methioninase is under free form or is pegylated, the delay is between about 1 h and about 7 days, between about 3 h and about 6 days, or between about 1 day and 5 days; and
   when methioninase is encapsulated into erythrocytes, the delay is between about 1 day and about 20 days, or between about 1 day and about 10 days.

2. The method of claim 1, wherein the methioninase comprises methioninase encapsulated inside erythrocytes and the asparaginase comprises asparaginase encapsulated inside erythrocytes, optionally wherein the erythrocytes have been encapsulated using a hypoosmotic encapsulation method.

3. The method of claim 2, wherein the delay between the end of the methioninase administration and the initiation of the asparaginase administration is between about 1 day and about 10 days.

4. The method of claim 2, wherein the methioninase is administered once or more in an amount of between about 100 and about 100,000 IU.

5. The method of claim 2, wherein the asparaginase is administered once or more in an amount of between about 500 and about 100,000 IU, or about 1,000 and about 50,000 IU.

6. The method of claim 2, wherein the methioninase is administered at least once or twice before the asparaginase is administered, and each methioninase administration is accompanied or followed by administration of PLP or a precursor of PLP before the asparaginase is administered.

7. The method of claim 6, wherein the non-phosphate precursor of PLP is administered once or more after each administration of methioninase.

8. The method of claim 7, wherein the non-phosphate precursor of PLP is administered once a day, or twice or more per day, during the time of each methioninase administration.

9. The method of claim 2, wherein the cancer is leukemia or gastric cancer, optionally wherein the composition further comprises at least one additional anticancer agent.

\* \* \* \* \*